United States Patent
Kim et al.

(10) Patent No.: US 11,738,064 B2
(45) Date of Patent: *Aug. 29, 2023

(54) PHARMACEUTICAL COMPOSITION FOR PREVENTING AND TREATING EYE DISEASES, CONTAINING AS ACTIVE INGREDIENT, FUSION PROTEIN IN WHICH TISSUE-PENETRATING PEPTIDE AND ANTI-VASCULAR ENDOTHELIAL GROWTH FACTOR PREPARATION ARE FUSED

(71) Applicant: ILDONG PHARM CO., LTD., Seoul (KR)

(72) Inventors: Seong Beom Kim, Gyeonggi-do (KR); Hyei Yoon Jung, Seoul (KR); Seok Woo Yang, Gyeonggi-do (KR); Hyuk Sang Kwon, Seoul (KR); Jae-Hoon Kang, Seoul (KR); Yong-Sung Kim, Gyeonggi-do (KR)

(73) Assignee: ILDONG PHARM CO., LTD., Seoul (KR)

(*) Notice: Subject to any disclaimer, the term of this patent is extended or adjusted under 35 U.S.C. 154(b) by 121 days.

This patent is subject to a terminal disclaimer.

(21) Appl. No.: 17/204,311

(22) Filed: Mar. 17, 2021

(65) Prior Publication Data

US 2021/0220436 A1  Jul. 22, 2021

Related U.S. Application Data

(63) Continuation of application No. 15/720,016, filed on Sep. 29, 2017, now Pat. No. 11,052,130, which is a continuation of application No. PCT/KR2016/003254, filed on Mar. 30, 2016.

(30) Foreign Application Priority Data

Mar. 31, 2015 (KR) .................. 10-2015-0045684

(51) Int. Cl.
| | |
|---|---|
| A61K 39/395 | (2006.01) |
| A61K 38/17 | (2006.01) |
| A61K 38/16 | (2006.01) |
| A61K 47/64 | (2017.01) |
| A61K 39/00 | (2006.01) |
| A61P 27/02 | (2006.01) |
| A61P 43/00 | (2006.01) |
| A61K 38/18 | (2006.01) |
| C07K 14/475 | (2006.01) |

(52) U.S. Cl.
CPC ............ *A61K 38/179* (2013.01); *A61K 38/16* (2013.01); *A61K 38/1866* (2013.01); *A61K 39/001135* (2018.08); *A61K 39/395* (2013.01); *A61K 47/64* (2017.08); *A61P 27/02* (2018.01); *A61P 43/00* (2018.01); *C07K 14/475* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 8,772,449 | B2 | 7/2014 | Morishita et al. |
| 9,975,933 | B2 | 5/2018 | Kim |
| 2007/0071756 | A1 | 3/2007 | Peyman |
| 2010/0322862 | A1 | 12/2010 | Ruoslahti et al. |
| 2013/0296238 | A1 | 11/2013 | Hohman |
| 2014/0193402 | A1 | 7/2014 | Wiegand et al. |
| 2016/0130315 | A1 | 5/2016 | Kim et al. |

FOREIGN PATENT DOCUMENTS

| | | |
|---|---|---|
| JP | 2013-541940 A | 11/2013 |
| JP | 2018515435 A | 6/2018 |
| KR | 1020110047196 | 5/2011 |
| KR | 10-2014-0138539 A | 12/2014 |
| KR | 10-1551299 | 9/2015 |
| WO | WO-2009/105669 A2 | 8/2009 |
| WO | WO 2009/136007 A1 | 11/2009 |
| WO | WO-2012/0033953 A1 | 3/2012 |
| WO | WO 2014/189303 A1 | 11/2014 |
| WO | WO 2016/159652 A1 | 10/2016 |

OTHER PUBLICATIONS

Felicity de Cogan, et al., "Topical Delivery of Anti-VEGF Drugs to the Ocular Posterior Segment Using Cell-Penetrating Peptides," Investigative Ophthalmology & Visual Science, May 2017, vol. 58, No. 5, pp. 2578-2590.
Krishna Radhakrishnan, et al. "Protein delivery to the back of the eye: barriers, carriers and stability of anti-VEGF proteins," Drug Discovery Today, Feb. 2017, vol. 22, No. 2, pp. 416-423.
Leslie N. Johnson, et al., "Cell-penetrating Peptide for Enhanced Delivery of Nucleic Acids and Drugs to Ocular Tissues Including Retina and Cornea," The American Society of Gene Therapy, Jan. 2008, vol. 16, No. 1, pp. 107-114.
Q. Sun, et al., "A Promising Future for Peptides in Ophthalmology: Work Effectively and Smartly", Current Medicinal Chemistry, 2015, 22, pp. 1030-1040.
Brazilian Preliminary Office Action in corresponding Brazilian Application No. BR112017020948-9, dated Sep. 1, 2020.
Johnson L N et al, "Cell penetrating peptide POD mediates delivery of recombinant proteins to retina, cornea and skin", Vision Research, Pergamon Press, Oxford, Mar. 31, 2010, GB, vol. 50, No. 7, ISSN 0042-6989, pp. 686-697, (Sep. 3, 2009), XP026964427 DOI: 10.1016/j.visres.2009.08.028.

(Continued)

*Primary Examiner* — Christine J Saoud
(74) *Attorney, Agent, or Firm* — LEASON ELLIS LLP

(57) ABSTRACT

The present invention relates to a pharmaceutical composition comprising, as an active ingredient, a fusion protein in which a tissue-penetrating peptide is fused to an anti-vascular endothelial growth factor agent, methods of treating eye diseases with the pharmaceutical composition, and a method for preparing an anti-VEGF agent with an improved efficacy and ability to overcome resistance.

9 Claims, 13 Drawing Sheets

Specification includes a Sequence Listing.

(56) References Cited

OTHER PUBLICATIONS

Johnson Leslie N et al, "Cell-penetrating peptide for enhanced delivery of nucleic acids and drugs to ocular tissues including retina and cornea", Molecular Therapy, Nature Publishing Group, Oct. 9, 2007, GB, vol. 16, No. 1, doi:10.1038/SJ.MT.6300324, ISSN 1525-0024, pp. 107-114, XP002521463 DOI: http://dx.doi.org/10.1038/SJ.MT.6300324.
Q. Sun et al, "A Promising Future for Peptides in Ophthalmology: Work Effectively and Smartly", Current Medicinal Chemistry, Feb. 16, 2015, NL, vol. 22, No. 8, doi:10.2174/0929867322666150114163308, ISSN 0929-8673, pp. 1030-1040, XP055513240 DOI: http://dx.doi.org/10.2174/0929867322666150114163308.
Sha, H. et al., "Tumor-penetrating Peptide Fused EGFR Single-domain Antibody enhances Cancer Drug Penetration into 3D Multicellular Spheroids and Facilitates Effective Gastric Cancer Therapy", Journal of Controlled Release, Dec. 30, 2014, vol. 200, pp. 188-200, XP029222013 DOI: http://dx.doi.org/10.1016/j.jconrel.2014.12.039.
Teesalu et al. "Tumor-penetrating peptides". Frontiers in Oncology. vol. 3, No. 216, pp. 1-8, Aug. 27, 2013. DOI: 10.3389/fonc.2013.00216 (#).
Kim et al. A brief history of anti-VEGF for the treatment of ocular angiogenesis. Am. J. Pathol. vol. 181, No. 2, pp. 376-379, Aug. 2012. DOI: 10.1016/j.ajpath.2012.06.006 (#).
Shin et al. Mol. Cancer Ther. 133): 651-661, 2014.
Johnson et al., "Cell penetrating peptide POD mediates delivery of recombinant proteins to retia, cornea and skin", Vision Res., Mar. 31, 2010, vol. 50, No. 7, pp. 686-697.
Oh et al. PNAS 99(1): 383-388, 2002.
JJ Chen, et al. "Potential penetration of topical ranibizumab (Lucentis) in the rabbit eye," Eye (2011) 25, pp. 1504-1511.
Qin Wang, et al., "Novel VEGF Decoy Receptor Fusion Protein Conbercept Targeting Multiple VEGF Isoforms Provide Remarkable Anti-Angiogenesis Effect In Vivo," PLOS One (Aug. 2013), vol. 8, Issue 8, e70544, 7 pages.
Basharut A. Syed, et al., "Wet AMD market," Nature Reviews (Nov. 2012), vol. 11, pp. 827-828.
Anja Lux, et al., "Non-responders to bevacizumab (Avastin) therapy of choroidal neovascular lesions," Br J Ophthalmol (2007), 91: pp. 1318-1322.
Steven A. Stacker et al., "A Mutant Form of Vascular Endothelial Growth Factor (VEGF) That Lacks VEGF Receptor-2 Activation Retains the Ability to Induce Vascular Permeability," The Journal of Biological Chemistry (Dec. 3, 1999), vol. 274, No. 49, pp. 34884-3892.
Taija Makinen, et al., "Differential Binding of Vascular Endothelial Growth Factor B Splice and Proteolytic Isoforms to Neuropilin-1," The Journal of Biological Chemistry (Jul. 23, 1999), vol. 274, No. 30, pp. 21217-21222.
Ralf H. Adams, et al., "The chemorepulsive activity of secreted semaphorins is regulated by furin-dependent proteolytic processing," The Embo Journal (1997), vol. 16, No. 20, pp. 6077-6086.
Tambet Teesalu, et al., "C-end rule peptides mediate neuropilin-1-dependent cell, vascular, and tissue penetration," PNAS, (Sep. 22, 2009), vol. 106, No. 38, pp. 16157-16162.
Matthew W. Parker, et al., "Structural Basis for Selective Vascular Endothelial Growth Factor-A (VEGF-A) Binding to Neuropilin-1," The Journal of Biological Chemistry (Mar. 30, 2012), vol. 287, No. 14, pp. 11082-11089.
Nobuo Jo, et al., "Inhibition of Platelet-Derived Growth Factor B Signaling Enhances the Efficacy of Anti-Vascular Endothelial Growth Factor Therapy in Multiple Models of Ocular Neovascularization," American Journal of Pathology (2006), vol. 168, No. 6, pp. 2036-2053.

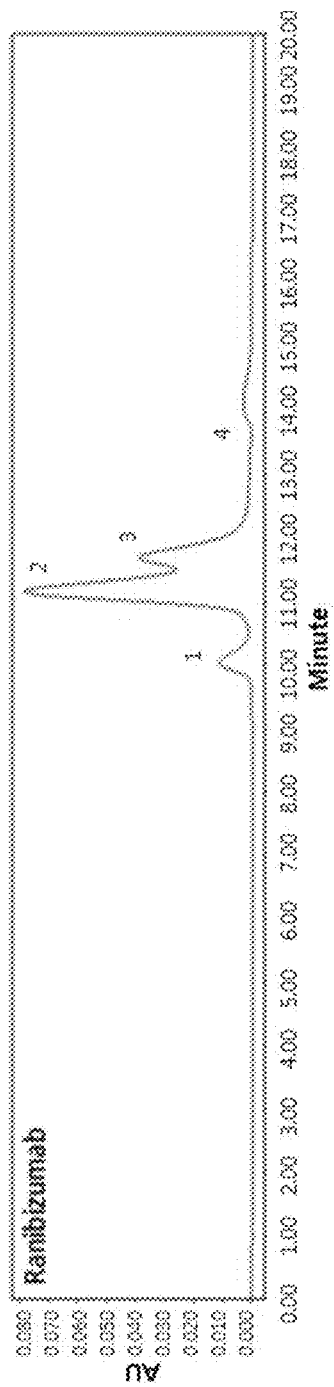
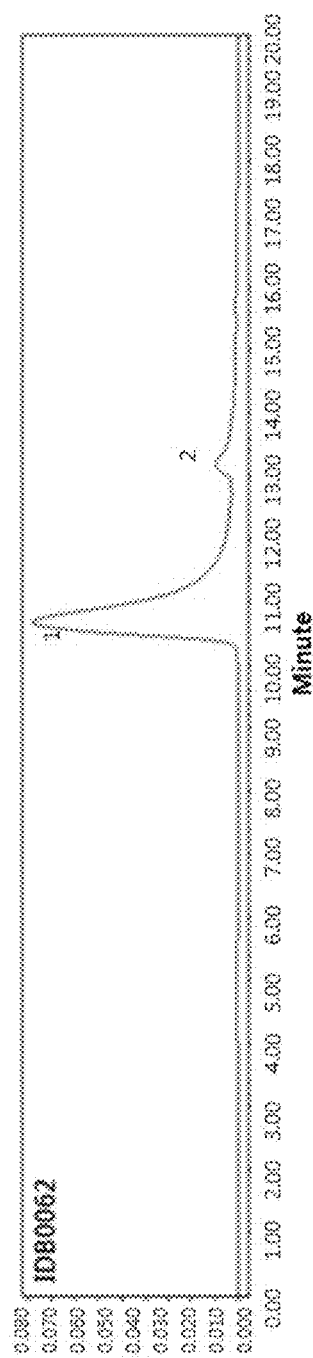
FIG. 2A
FIG. 2B

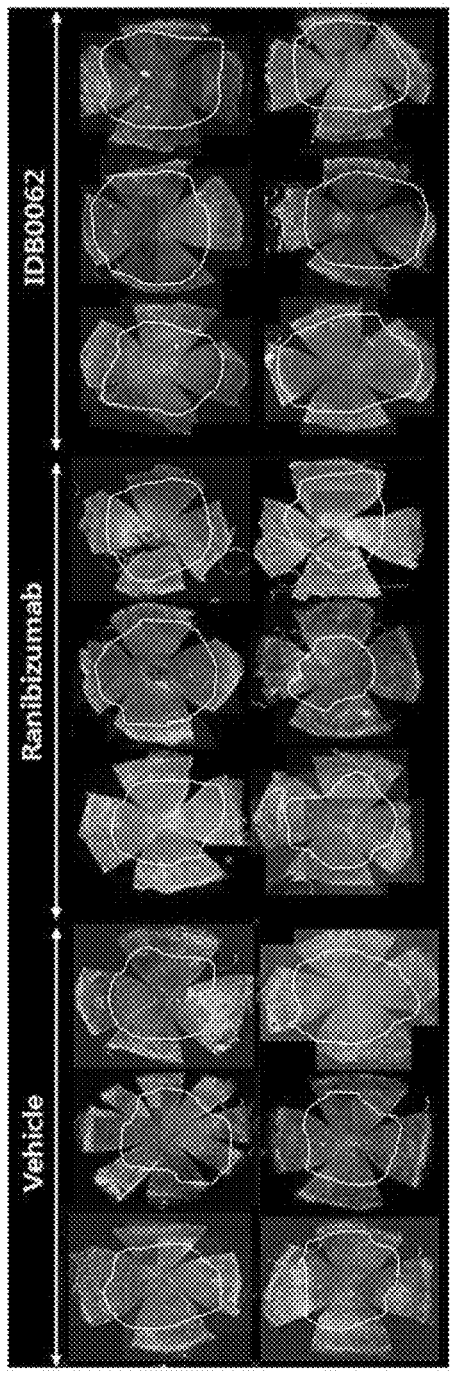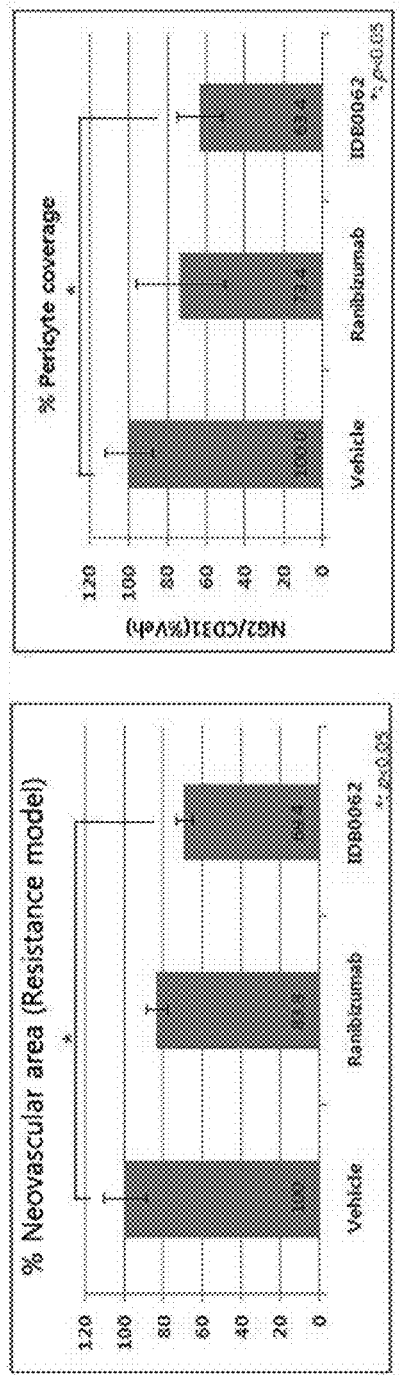
FIG. 7A
FIG. 7B
FIG. 7C

PHARMACEUTICAL COMPOSITION FOR PREVENTING AND TREATING EYE DISEASES, CONTAINING AS ACTIVE INGREDIENT, FUSION PROTEIN IN WHICH TISSUE-PENETRATING PEPTIDE AND ANTI-VASCULAR ENDOTHELIAL GROWTH FACTOR PREPARATION ARE FUSED

CROSS-REFERENCE TO RELATED APPLICATIONS

The present application is a continuation of U.S. application Ser. No. 15/720,016, filed Sep. 29, 2017, which is a continuation of International Application No. PCT/KR2016/003254, filed on Mar. 30, 2016, which claims priority to Korean Patent Application No. 10-2015-0045684 filed on Mar. 31, 2015, which are hereby incorporated in its entirety by reference.

JOINT RESEARCH AGREEMENT

The present disclosure was made by or on behalf of the below listed parties to a joint research agreement. The joint research agreement was in effect on or before the effective filing date of the present disclosure and the present disclosure was made as a result of activities undertaken within the scope of the research agreement. The parties to the joint research agreement are 1) ILDONG PHARM CO., LTD. and 2) AJOU UNIVERSITY-INDUSTRY ACADEMIC COOPERATION FOUNDATION.

INCORPORATION BY REFERENCE OF SEQUENCE LISTING

The instant application contains a Sequence Listing which has been submitted electronically in ASCII format and is hereby incorporated by reference in its entirety. Said ASCII copy, created on Nov. 4, 2019, is named 02707581.txt and is 38,881 bytes in size.

TECHNICAL FIELD

The present invention relates to a pharmaceutical composition for preventing and treating an eye disease, the composition comprising, as an active ingredient, a fusion protein in which a tissue-penetrating peptide is fused to an anti-vascular endothelial growth factor (anti-VEGF) agent. More specifically, the present invention relates to a pharmaceutical composition for preventing and treating an eye disease, the composition comprising, as an active ingredient, a fusion protein in which a tissue-penetrating peptide is fused to an anti-VEGF agent. The present invention also relates to a method for preparing an anti-VEGF agent with an improved efficacy and ability to overcome resistance, the method comprising: transforming host cells with a recombinant vector, the recombinant vector containing a nucleic acid sequence encoding a fusion protein in which a tissue-penetrating peptide is fused to an anti-VEGF agent; culturing the cells; and collecting a fusion protein from the cells. The present invention further relates to a method for treating an eye disease, the method comprising administering an effective amount of the fusion protein according to the present invention to a subject in need thereof; and to a use of the fusion protein according to the present invention for preparing an eye disease therapeutic agent comprising the fusion protein as an active ingredient.

BACKGROUND ART

While macula lutea is a part of the retina of the eye in which visual cells are concentrated to receive light most clearly and accurately, and a disease that causes visual impairment by the degeneration of the macula lutea occurring due to various causes is called macular degeneration. The macular degeneration is one of the three causes of blindness, together with glaucoma and diabetic retinopathy. The greatest cause of macular degeneration is an increase in age, while family history, race, smoking, and the like are also known as causes of macular degeneration. Damage to the macula lutea will cause the loss of the ability to recognize details, such as small prints, facial features, or small objects. This macular degeneration has two types: non-exudative (dry) macular degeneration and exudative (wet) macular degeneration, while the prevalence of dry macular degeneration is 90%. In dry macular degeneration, wastes form yellow precipitates, called drusen, which may accumulate in the tissue below macular tissue. The presence of drusen interferes with blood flow to the retina, especially the macula lutea, and the reduced blood flow reduces the supply of nutrients to the macula lutea, stopping or constricting efficient actions of photosensitive cells. As for wet macular degeneration, new weak blood vessels grow in or under the retina, causing fluid and blood to leak into the space below the macula. Wet macular degeneration is sometimes described as choroidal neovascularization. The choroid is a vascular region below the macula lutea and neovascularization refers to the growth of new blood vessels in the tissue. As can be inferred from the name of the choroidal neovascularization, with respect to wet macular degeneration, blood vessels are newly formed to grow from the choroid to the macula lutea. This macular degeneration was considered to be a disease for elderly people, but in recent years, patients in their 40s and 50s are known to be rapidly increasing. The main causes of this decrease in age at onset of macular degeneration are westernization of eating habits, such as an increase in fat intake, and unfavorable habits, such as smoking, drinking, and exposure to ultraviolet rays.

Diabetic macular edema (DME) is explained by the thickening of the retina and/or hard exudate within one disc diameter from the center of the retina. DME and diabetic retinopathy (DR) are microvascular complications occurring in diabetic patients, and weaken eyesight and eventually result in blindness. The patients with DR show a progression of DME, and dilated hyperpermeable capillaries and microaneurysm leakage may cause DME after the breakdown of blood-retinal barriers. Similar to DR, DME is associated with choroidal neovascularization that penetrates damaged or tissue-destroyed Bruch's membranes.

Meanwhile, examples of a typical medication that is used for the prevention or treatment of various eye diseases associated with neovascularization in eyes (such as the macular degeneration and diabetic macular edema) include ranibizumab, bevacizumab, aflibercept, conbercept, and the like. Currently developed biopharmaceuticals, including the foregoing medications, for the treatment of major eye diseases, such as macular degeneration and diabetic retinopathy edema, are mainly used to treat diseases of posterior eyeballs, including the retina, in the form of an intraocular injection. Recently, attempts have been made to develop a form of eye drops of ranibizumab, aflibercept and the like in order to solve such problems as reduced patient convenience, increased side effects, and psychological fear of injections. However, as shown in the test results that ranibizumab reached the retinal tissue 3-7 days after a half-dose (250 µg) of ranibizumab is dropped in the eyes 6 times at 2 hour intervals in rabbits (Chen et al., 2011. Eye), ranibizumab has a poor ocular permeability and a difficulty in reaching the posterior part of the eyeball where the lesion is present, while a large amount of drug is lost due to aqueous outflow by eye blinking at the time of applying the eye drops, and thus, its pharmaceutical effect in the form of eye drops is difficult to achieve in the eyes. In addition, similar to aflibercept, conbercept (Chengdu Kanghong pharm.), which was approved as a therapeutic agent for macular degeneration in 2013, is a fusion protein in which the second domain of vascular endothelial growth factor receptor-1 (VEGFR-1) is linked to the third and fourth domains of VEGFR-2 via Fc, and is also being currently developed as an eye drop dosage form. However, according to the reports, conbercept has a bioavailability of less than about 5% at the time of applying its eye drops (Wang et al., 2013. PLOS ONE).

In addition, ranibizumab, which is marketed under the trade name Lucentis, has received attention since about 90% of patients with macular degeneration showed response at the time of development. However, only 30% of responding patients showed a therapeutic effect, such as eyesight improvement, and its continuous administration caused drug resistance (Syed et al., 2012. Nature Rev. Drug Discov.). In order to improve such shortcomings, aflibercept, which is an Fc fusion antibody designed to have a 100-fold increase in binding ability to VEGF-A and to be able to inhibit even VEGF-B and PlGF, had been released in 2011 and showed a significant commercial growth, but, actually, it has been confirmed that the two products have no difference in a clinical efficacy.

About 10% of patients with macular degeneration are unresponsive to anti-VEGF agents, and thus, the therapeutic effect thereof to such patients cannot be expected. This is thought to be due to other growth factor-dependent neovascular bypass other than VEGF-A. In addition, it has been confirmed that repeated administrations caused resistance in about 45% of patients, and drug response decreases as the number of administration increases (Lux et al., 2007. Br. J. Ophthalmol.). This resistance is known to be caused by vascular strengthening resulting from increased pericyte coverage that contributes to stabilization of endothelial cells at the time of repeated administrations of anti-VEGF agent and pericyte-dependent VEGF production.

Therefore, the recent development trend of eye disease therapeutic agents is to develop a combination therapy using a PDGF inhibitor for inducing pericyte dissociation in order to overcome resistance and improve efficacy of anti-VEGF agents. Therefore, an eye disease therapeutic agent capable of: (i) adding a function of blocking VEGF-A and other neovascularization-related ligands; (ii) overcoming resistance to an anti-vascular endothelial growth factor agent; (iii) disrupting pericyte coverage to improve drug efficacy; (iv) improving the frequency of administration; and (v) being developed as eye drops.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows the HPLC analysis results of major products by the production of ranibizumab. FIG. 2B shows the HPLC analysis results of major products by the production of the fusion protein of the present invention (IDB0062: Fab fusion protein in which tissue-penetrating peptide TPP #2 is fused to a ranibizumab mutant). AU means an arbitrary unit.

FIG. 7A shows the evaluation results of vascularization inhibitory effect of ranibizumab and a fusion protein according to the present invention in corneal neovascularization resistance models. FIG. 7B is a graph obtained by quantifying the results of FIG. 7A. FIG. 7C shows the evaluation results of pericyte coverage reduction effect of ranibizumab and a fusion protein according to the present invention.

DETAILED DESCRIPTION OF THE INVENTION

Technical Problem

Figure 1A:
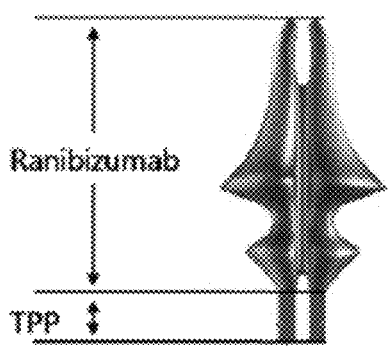
FIG. 1A is a schematic diagram of a fusion protein in which a tissue-penetrating peptide is fused to an anti-vascular endothelial growth factor antigen-binding fragment (Fab).

The present inventors have found that a fusion of an anti-vascular endothelial growth factor (anti-VEGF) agent and a tissue-penetrating peptide increases the tissue penetration of drug, disrupts pericyte coverage to exert its effect on even a patient showing resistance to drug, reduces the dose or improves the frequency of administration, and allows a development as eye drops, and then completed the present invention.

Therefore, an aspect of the present invention is to provide a pharmaceutical composition for preventing and treating an eye disease, the composition comprising, as an active ingredient, a fusion protein in which a tissue-penetrating peptide is fused to an anti-vascular endothelial growth factor (anti-VEGF) agent.

Another aspect of the present invention is to provide a method for preparing an anti-vascular endothelial growth factor (anti-VEGF) agent with an improved efficacy and ability to overcome resistance, the method comprising: (a) transforming host cells with a recombinant vector, the recombinant vector including a nucleic acid sequence encoding a fusion protein in which a tissue-penetrating peptide is fused to an anti-vascular endothelial growth factor (anti-VEGF) agent; (b) culturing the cells; and (c) collecting a fusion protein from the cells.

Still another aspect of the present invention is to provide a method for treating an eye disease, the method comprising administering an effective amount of a fusion protein, in which a tissue-penetrating peptide is fused to an anti-vascular endothelial growth factor (anti-VEGF) agent, to a subject in need thereof.

Still another aspect of the present invention is to provide a use of a fusion protein in which a tissue-penetrating peptide is fused to an anti-vascular endothelial growth factor (anti-VEGF) agent for preparing an eye disease therapeutic agent comprising the fusion protein as an active ingredient.

Technical Solution

In accordance with an aspect of the present invention, there is provided a pharmaceutical composition for preventing and treating an eye disease, the composition comprising, as an active ingredient, a fusion protein in which a tissue-penetrating peptide is fused to an anti-vascular endothelial growth factor (anti-VEGF) agent.

In accordance with another aspect of the present invention, there is provided a method for preparing an anti-vascular endothelial growth factor (anti-VEGF) agent with an improved efficacy and ability to overcome resistance, the method comprising: (a) transforming host cells with a recombinant vector, the recombinant vector including a nucleic acid sequence encoding a fusion protein in which a tissue-penetrating peptide is fused to an anti-vascular endothelial growth factor (anti-VEGF) agent; (b) culturing the cells; and (c) collecting a fusion protein from the cells.

In accordance with still another aspect of the present invention, there is provided a method for treating an eye disease, the method comprising administering an effective amount of a fusion protein, in which a tissue-penetrating peptide is fused to an anti-vascular endothelial growth factor (anti-VEGF) agent, to a subject in need thereof.

In accordance with still another aspect of the present invention, there is provided a use of a fusion protein in which a tissue-penetrating peptide is fused to an anti-vascular endothelial growth factor (anti-VEGF) agent for preparing an eye disease therapeutic agent comprising the fusion protein as an active ingredient.

Hereinafter, the present invention will be described in detail.

In accordance with an aspect of the present invention, there is provided a pharmaceutical composition for preventing and treating an eye disease, the composition comprising, as an active ingredient, a fusion protein in which a tissue-penetrating peptide is fused to an anti-vascular endothelial growth factor (anti-VEGF) agent.

Vascular endothelial growth factor-A (VEGF-A) among the proteins present in nature is well known to induce blood extravasation. This is also called a vascular permeability factor. This action is known to be due to its combination with a vascular endothelial growth factor receptor (VEGFR2), but interestingly, the mutation experiment of vascular endothelial growth factor-A showed that the vascular penetration of vascular endothelial growth factor-A was increased even though vascular endothelial growth factor-A did not bind to the vascular endothelial growth factor receptor. This suggested that there is another receptor for vascular endothelial growth factor-A (Stacker et al., 1999. J. Biol. Chem.). Other contemporary researchers established that this receptor is neuropilin (NRP) (Makinen et al., 1999. J. Biol. Chem.).

Neuropilin was first found in the *Xenopus* nervous system. Neuropilin is a transmembrane glycoprotein, and has two types: NRP1 and NRP2. Neuropilin acts as a coreceptor for VEGF receptors (VEGFRs) by VEGF family ligand binding. In particular, NRP1 binds to various VEGF ligands by acting as a co-receptor for VEGFR1, VEGFR2, and VEGFR3. On the other hand, NRP2 contributes to lymphangiogenesis and cell adhesion by acting as a co-receptor for VEGFR2 and VEGFR3. In addition, NRP1/NRP2 (NRP1/2) act as a co-receptor for the Plexin family receptors and bind to secreted class 3 semaphorin ligands (Sema3A, Sema3B, Sema3C, Sema3D, Sema3E, Sema3F and Sema3G).

As used herein, the term "tissue penetrating" or "tissue penetration" means having any one characteristic of: specifically recognizing tissues overexpressing neuropilin to be accumulated in the tissues; widening the cell gap between vascular endothelial cells to promote drug extravasation; or promoting the drug distribution in the eye by adjusting the gap between corneal cells, which are a tissue acting as a barrier against water-soluble molecules.

As used herein, the term "neuropilin (NRP)" refers to a transmembrane glycoprotein, and has two types: NRP1 and NRP2. Neuropilin is largely composed of five domains. From the N-terminus, a1/a2 domains are classified as CUB domains which an Ig-like C2 type domain of semaphorin binds thereto. Especially, these domains form a complex with plexin to increase binding ability with semaphorin-plexin. The b1 and b2 domains of neuropilin are classified as FV/VIII domains which the C-termini of VEGF family ligands or secreted class 3 semaphorin ligands (Sema3s) bind thereto. The VEGF ligands and class 3 semaphorin ligands have a recognition site (RXRR, Arg-X-Arg-Arg, SEQ ID NO: 43)

of furin protease, and thus the ligands commonly end with an arginine (Arg) amino acid residue at the C-terminus by furin processing (Adams et al., 1997. EMBO J.). It has been reported that the Arg residue at the C-terminus of the VEGF and Sema3s ligands is very important in the interaction of neuropilin b1b2 domains (Teesalu et al., 2009. Proc. Natl. Acad. Sci. USA). The tertiary structure of a complex between the VEGF ligand and the neuropilin b1b2 domain has been revealed (Parker et al., 2012. J. Biol. Chem.), and accordingly, the amino acid sequence of VEGF, which is important in the binding to the neuropilin b1b2 domain, can be recognized. However, it still has not been established which site of the C-terminus of Sema3A binding to NRP1 specifically binds to NRP.

The anti-vascular endothelial growth factor agent includes a molecule that interferes with an interaction between VEGF and a natural VEGF receptor, for example, a molecule that binds to VEGF or a VEGF receptor to prevent or interfere with an interaction between VEGF and VEGF receptor. Examples of the VEGF antagonist include anti-VEGF antibodies, anti-VEGF receptor antibodies, and VEGF receptor-based chimeric molecules.

As used herein, the term "fusion" refers to integrating two molecules each possessing the same or different functions or structures, and may be a fusion by any physical, chemical, or biological method whereby a tissue-penetrating peptide can bind to an anti-vascular endothelial growth factor agent. The fusion may be preferably by a linker peptide, while this linker peptide may bind to, for example, the C-terminus of Fab (antigen-binding fragment) or Fc fragment in an antibody.

The eye disease of the present invention preferably means an eye disease by neovascularization. As used herein, the expression "eye disease by neovascularization" refers to any eye disease by vascular growth or proliferation, vascular leakage, or those associated therewith.

The fusion protein according to the present invention increases the tissue penetration of drug by binding to a neuropilin receptor, disrupts pericyte coverage to exert its effect on even a patient showing resistance to drug, improves the frequency of administration, and allows its development as eye drops.

Specifically, according to an Example of the present invention, a ranibizumab mutant having a point mutation in which cysteine (C) is substituted with serine (S) in the amino acid sequence of ranibizumab significantly increased productivity, while a modified form in which a tissue-penetrating peptide (TPP) is fused to the ranibizumab mutant also maintained the increased productivity intact (Example 1).

According to another Example of the present invention, as a result of comparison of the affinity to neuropilin receptor and the disruption ability of tight junction between endothelial cells of a fusion protein in which a tissue-penetrating peptide was fused to the C-terminus of the ranibizumab mutant, it was confirmed that the fusion protein very favorably bound to neuropilin receptor NRP1 and Sema3A ligand at similar levels, and remarkably inhibited VE-cadherin, indicating its significantly excellent disruptive ability of tight junctions between endothelial cells (Example <1-3>).

According to another Example of the present invention, in order to investigate whether the fusion protein in which a tissue-penetrating peptide is fused to the C-terminus of a ranibizumab mutant can improve the penetration by binding with neuropilin receptors distributed widely in ocular endothelial cells, the extracted eyeballs were immersed in a solution comprising the fusion protein and a solution containing ranibizumab and then the penetration over time was compared therebetween (Example 4). The experiment results confirmed that an anti-vascular endothelial growth factor agent binding to the tissue penetrating peptide initiated the penetration from the corneal epithelial tissues from one hour after the experiment and showed a significantly high drug distribution in the eye within 2 hours compared with ranibizumab, and thus, confirmed the possibility of controlling the dose and increasing the interval of administration through the improvement of penetration.

That is, it could be verified that, compared with the previous study that the ocular penetration of ranibizumab was significantly low, the fusion protein according to the present invention penetrated the cornea, which serves as a barrier against water-soluble molecules, more rapidly than ranibizumab, and reached the inside of the eyeball. Thus, the fusion protein according to the present invention has a possibility of being developed as eye drops through the improvement of formulation in the future. The effect of increasing the ocular tissue penetration through the fusion with the tissue-penetrating peptide was similarly observed in the whole antibody form with a large molecular weight and a complicated protein structure, as well as in a Fab-type ranibizumab modified form. A fusion protein in which a tissue-penetrating peptide is fused to the Fc-terminus of immunoglobulin G (IgG) type bevacizumab also showed a significantly increased ocular penetration ability compared with bevacizumab, indicating that a bevacizumab modified form according to the present invention can also be developed as a drug with an increased therapeutic effect.

It can be predicted from the results of the present Examples that, similar to bevacizumab, aflibercept, conbercept and the like in a fusion protein form in which VEGF receptors (VEGFR1 and VEGFR2) are fused to an Fc fragment, if a tissue-penetrating peptide is fused to the Fc-terminus, can also be developed as drugs with a remarkably enhanced therapeutic effect, compared with existing Fc fusion proteins.

In another Example of the present invention, the neovascularization inhibitory effect and the neovascularization inhibitory effect in drug resistance models were compared and evaluated using various animal disease models between the fusion protein of the present invention and ranibizumab. As a result of experiment using corneal neovascularization models, the fusion protein of the present invention showed a significant neovascularization inhibitory effect of 50% or more compared with a control group and an equivalent effect to ranibizumab, confirming an improvement in efficacy by the tissue-penetrating peptide fused to the C-terminus (Example <5-1>). In addition, as for the neovascularization inhibitory effect in drug resistance models, the fusion protein of the present invention showed an excellent efficacy by two times or more compared with ranibizumab, while this value is similar to the results in a literature disclosing a co-administration of anti-VEGF aptamer and anti-PDGF antibody agent (Jo et al., 2006. Am. J. Pathol. 168), and thus, it can be predicted that the fusion protein of the present invention has a possibility of eyesight improvement in about 70% of the patients administered with ranibizumab, of which eyesight was only maintained without eyesight improvement (Example <5-2>). The excellent effect of inhibiting neovascularization in the eye disease by the fusion protein according to the present invention was also observed similarly in a choroidal neovascularization (CNV) model used as an actual macular degeneration efficacy model and an oxygen-induced retinopathy (OIR) used as a retinopathy efficacy model, and thus, it can be predicted that the fusion protein of the present invention has a clinically remarkably increased therapeutic effect, compared with ranibizumab (Example 6 and Example 7).

As used herein, the term "prevention" refers to all acts of suppressing an eye disease or delaying the progress of an eye disease by administering a composition of the present invention.

As used herein, the term "treatment" refers to all acts of improving or beneficially changing an eye disease by administering a composition of the present invention. More specifically, the term "treatment" refers comprehensively to ameliorating symptoms of an eye disease, which may encompass healing, substantially preventing, or ameliorating the condition of an eye disease, and may encompass ameliorating, healing, or preventing one symptom or most of the symptoms resulting from an eye disease, but is not limited thereto.

In practicing the present invention, a person skilled in the art can determine an effective dose (effective amount), the number of administrations, and the route of administration in order to prevent or treat an eye disease, upon properly considering various factors, such as a type and severity of the corresponding eye disease, the age, weight, health condition, sex, diet, and excretion rate of the subject in need of administration. The term "effective amount" comprehensively refers to an amount to improve symptoms of an eye disease when administered to a subject, and encompasses an amount to heal or substantially prevent an eye disease or ameliorate the condition of an eye disease. The term "subject" may be an animal, preferably a mammal, and especially, an animal including a human being, and may include cells, tissues, organs, or the like which are derived from an animal. The subject may be a patient in need of treatment. The composition of the present invention may be administered to mammals including humans by any methods. For example, the composition of the present invention may be administered orally or parenterally. The parental administration may be, but is not limited to, intravenous, intramuscular, intra-arterial, intramedullary, intradural, intracardiac, transdermal, subcutaneous, intraperitoneal, intranasal, intestinal, topical, sublingual, or rectal administration. An immunogenic complex protein according to the present invention may be administered alone or in combination with a known compound having an effect of preventing and treating a target disease.

For example, the dose of the pharmaceutical composition of the present invention to the human body may vary depending on the age, weight, sex, dosage form, health condition, and disease severity of a patient. For ocular injection, the dose may be generally 0.001-10 mg/day per eyeball, and preferably, 0.1-2 mg/day per eyeball. For eye drops, the dose may be 0.001-100 mg/day and preferably 0.01-10 mg/day per 1 ml of an eye drop solution. The composition may also be divisionally administered at predetermined intervals according to the determination of a physician or pharmacist.

The composition of the present invention may further contain a pharmaceutically acceptable additive. Examples of the pharmaceutically acceptable additive may include starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxymethyl starch, carunauba wax, synthetic aluminum silicate, stearic acid, magnesium stearate, aluminum stearate, calcium stearate, white sugar, dextrose, sorbitol, talc, etc. The pharmaceutically acceptable additive according to the present invention is preferably contained in 0.1-90 weight part relative to the pharmaceutical composition.

In addition, the pharmaceutical composition may be in various forms suitable for any route of administration, including, but not limited to, an injection, eye drops, eye ointment, and an intraocular dosage form. In cases where the pharmaceutical composition is formulated, diluents or excipients, such as a filler, an extender, a binder, a wetting agent, a disintegrant, or a surfactant, may be used. The injection may include all of intravitreal injection and intraocular local injection including conjunctival injection, but is not limited thereto. The injection may contain conventional additives, such as a solubilizer, an isotonic agent, a suspending agent, an emulsifier, a stabilizer, and a preservative.

Suitable carriers for the injection of the present invention include physiological saline, bacteriostatic water, Cremophor EL (BASF, Parsippany, N.J., USA) or phosphate buffered saline (PBS). In all cases, the composition must be sterile and should be fluid to the extent that easy syringability exists. The composition must be stable under the conditions of manufacture and storage, and must be preserved against the contaminating action of microorganisms such as bacteria and fungi. The carrier may be a solvent or dispersion medium containing, for example, water, ethanol, polyol (for example, glycerol, propylene glycol, and liquid polyethylene glycol, and the like), and suitable mixtures thereof. The proper fluidity may be maintained, for example, by the use of a coating such as lecithin, by the maintenance of the required particle size in the case of a dispersion, and by the use of surfactants. Prevention of the action of microorganisms can be brought about by various antibacterial and antifungal agents, for example, parabens, chlorobutanol, phenol, ascorbic acid, thimerosal, and the like. In many cases, the composition will be preferable to contain isotonic agents, for example, sugars, polyalcohols, such as mannitol or sorbitol, or sodium chloride. Prolonged absorption of the injectable compositions can be brought about by including in the composition an agent which delays absorption, for example, aluminum monostearate, hyaluronic acid, and gelatin.

The eye drops may be a water-soluble ophthalmic solution, a water-insoluble ophthalmic solution, or an ophthalmic emulsion. The eye drops of the present invention may contain, in addition to a fusion protein in which the above essential component, tissue-penetrating peptide, is fused to the anti-vascular endothelial cell growth factor (anti-VEGF) agent, any conventionally known component in the eye drops, for example, a buffer, a viscosity controlling agent, a stabilizer, an isotonic agent, a preservative, and the like, may be mixed with the fusion protein. Of these, examples of the buffer may include known buffers of citrate, phosphate, acetate, and amino acid salts. In addition, examples of the viscosity controlling agent may include polyvinyl alcohol, hydroxypropylcellulose, methylcellulose, povidone, hydroxypropyl methylcellulose, ethylcellulose, hydroxyethylcellulose, carmellose, polyethylene glycol, chondroitin, or salts thereof. Examples of the stabilizer may include: antioxidants, such as sodium nitrite, sodium hydrogen sulfite, and sodium metabisulfite; and chelating agents, such as sodium edetate, cyclodextrin, citric acid, and citrate. In addition, examples of the isotonizing agent may include: salts, such as sodium chloride and potassium chloride; polyhydric alcohols, such as glycerin and propylene glycol; sugars, such as glucose, sucrose, and trehalose; sugar alcohols, such as xylitol and sorbitol; polyethers, such as polyethylene glycol; and amidosulfonic acids, such as taurine. In addition, examples of the preservative may include benzalkonium chloride, benzethonium chloride, chlorobutanol, paraoxybenzoic ester, thimerosal, sorbic acid, sorbate, chlorhexidine gluconate, and the like. In the eye drops of the present invention, the pH at room temperature is preferably 4.5-8.5, more preferably 5.5-8, and particularly preferably 6-8. The pH is measured at room temperature using a pH meter (e.g., Accumet model 25 pH/Ion meter manufactured by Fisher Scientific).

Some ophthalmic drugs cannot be administered as eye drops since they have poor permeability through the eye barrier. Therefore, ointment can be used to extend the contact time and increase the amount of drug absorbed. Examples of the water-insoluble polymer as a carrier component which can be used in eye drops may include ethyl cellulose, an ethylene-vinyl acetate copolymer, polymethyl methacrylate, an ethyl acrylate-methyl methacrylate-trimethylammonium ethyl chloride methacrylate copolymer, and a methyl methacrylate-butyl methacrylate-dimethyl aminoethyl methacrylate copolymer, and the like. Examples of the biodegradable polymer may include polylactic acid, a polylactic acid-glycolic acid copolymer, polycyanoacrylate, polyalkyl cyanoacrylate, poly-ε-caprolactone, and the like. Examples of the water-soluble polymer may include: cellulose derivatives, such as hydroxypropylmethyl cellulose phthalate, carboxymethylethyl cellulose, and hydroxypropyl cellulose; calcium alginate, chitosan, albumin, gelatin, a methacrylic acid-methyl methacrylate copolymer, and the like. Examples of an oily component may include tripalmitine, cetyl alcohol, cholesterol, various phospholipids, cetyl palmitate, cholesterol palmitate, and the like. These carrier components usually have an ability to sustained-release an active component comprising an active substance for ophthalmic therapy. A carrier component with high specific gravity that is usable without addition of any specific gravity modified form may be, for example, hydroxypropyl methyl cellulose phthalate 200731 (specific gravity: 1.65), hydroxypropyl methyl cellulose phthalate 220824 (specific gravity: 1.82), carboxymethyl ethyl cellulose (specific gravity: 1.59) and the like. Nevertheless, even when such a carrier component is used, it is preferable to add a specific gravity modified form to further increase the specific gravity. In the present invention, examples of the specific gravity modified form used for adjusting the specific gravity of carrier particles may include, but are not limited to: insoluble components, such as titanium oxide (specific gravity: 4.17); hardly soluble components, such as tricalcium phosphate (specific gravity: 3.14), anhydrous calcium hydrogen phosphate (specific gravity: 2.89), and calcium hydrogen phosphate dehydrate (specific gravity: 2.30); water-soluble components, such as sodium chloride (specific gravity: 2.17), potassium chloride (specific gravity: 1.98), calcium chloride (specific gravity: 2.0), magnesium chloride (specific gravity: 2.41), sodium carbonate (specific gravity: 2.53), sodium dihydrogen phosphate (specific gravity: 1.95), sodium monohydrogen phosphate (specific gravity: 1.7), and potassium dihydrogen phosphate (specific gravity: 2.34).

An insert is generally similar to a soft contact lens placed in the cornea, except that the insert is placed in the upper cul-de-sac rather than attached to the open cornea, or less frequently in the lower conjunctival sac. The insert is typically manufactured of a biologically soluble material that dissolves or disintegrates in the lachrymal fluid while releasing the drug.

Solid preparations for oral administration may include a tablet, a pill, a powder, a granule, a capsule, and the like. These solid preparations may be prepared by mixing tyrosol with at least one excipient, for example, starch, calcium carbonate, sucrose, lactose, gelatin, or the like. In addition to simple excipients, lubricants, such as magnesium stearate and talc, may be used. Liquid preparations for oral administration include a suspension, a liquid for internal use, oil, syrup, and the like, and may also include, in addition to simple diluents, such as water and liquid paraffin, several excipients, for example, a wetting agent, a sweetener, an aroma, a preservative, and the like.

In addition, the therapeutic composition of the present invention may further contain any physiologically acceptable carrier, excipient, or stabilizer (Remington: The Science and Practice of Pharmacy, 19th Edition, Alfonso, R., ed, Mack Publishing Co. (Easton, Pa.: 1995)). The acceptable carrier, excipient, or stabilizer is non-toxic to a user at used dose and concentration, and examples thereof include: buffers, for example, phosphoric acid, citric acid, and other organic acids; antioxidants including ascorbic acids; low-molecular weight (less than about 10 residues) polypeptides; proteins, for example, serum albumin, gelatin, or immunoglobulin; hydrophilic polymers, for example, polyvinyl pyrrolidone; amino acids, for example, glycine, glutamine, asparagine, arginine, or lysine; monosaccharides, disaccharides, and other carbohydrates, including glucose, mannose, or dextrin; chelating agents, for example, EDT; sugar alcohols, for example, mannitol or sorbitol; salt-forming counter ions, for example, sodium; and (or) non-ionic surfactants, for example, Tween, pluronics, or polyethylene glycol (PEG).

In accordance with another aspect of the present invention, there is provided the pharmaceutical composition wherein the tissue-penetrating peptide includes any one amino acid sequence selected from the group consisting of SEQ ID NOs: 1 to 7.

The tissue-penetrating peptide represented by an amino acid sequence selected from SEQ ID NOs: 1 to 7 is designed based on the fact that the amino acid sequence of a binding region of $VEGF_A$ ligand, which binds to b1b2 domain of neuropilin, and the length of the amino acid sequence are analyzed, and the nucleotide sequences of furin C-terminus sequences of semaphorin 3A and semaphorin 3F, which are known to bind to neuropilin, are analyzed, and thus the sequences of the C-terminus thereof are similar to each other.

According to another aspect of the present invention, the present invention provides a pharmaceutical composition wherein the anti-vascular endothelial growth factor agent includes: an agent used to prevent or treat an eye disease and selected from the group consisting of bevacizumab, ranibizumab, r84 (PLoS One. 2010 Aug. 6; 5(8)), aflibercept, conbercept, CT01 (WO2005056764A2), DOM15-10-11 (WO2008149147A2), DOM15-26-593 (WO2008149143A2), PRS-050 (Mross et al., 2013. PLoS One), CT-322 (Dineen et al., 2008. BMC Cancer), ESBA903 (Asmus et al., 2015. Eur J Pharm Biopharm.), and EPI-0030 (WO2011023130A1); biosimilars thereof, and mutants thereof. More preferably, the anti-vascular endothelial growth factor agent may be ranibizumab, bevacizumab, aflibercept, or conbercept, but is not limited thereto.

As used herein, the term "biosimilar" refers to a copy medical product that is verified to have equivalence in light of quality, efficacy, and safety by mimicking an off-patent original biological medical product that has already been developed/marketed by using biotechnology (such as gene recombination and cell culture technology).

In accordance with another aspect of the present invention, there is provided a pharmaceutical composition wherein the mutant may be one in which cysteine is deleted, or substituted with another amino acid residue including serine excluding cysteine in heavy chain constant domain and light chain constant domain.

In an Example of the present invention, a ranibizumab mutant in which the last residue cysteine is substituted with serine in the nucleotide sequence of ranibizumab was constructed by a protein engineering method using the conversion of the amino acid sequence of ranibizumab (Example <1-1>).

In accordance with another aspect of the present invention, there is provided the pharmaceutical composition, wherein the mutant is a ranibizumab mutant consisting of a light chain represented by SEQ ID NO: 8 and a heavy chain represented by SEQ ID NO: 10.

The tissue-penetrating peptide according to an aspect of the present invention may further include a linker peptide. The linker peptide may be composed of 1 to 50 amino acids, preferably 4 to 20 amino acids, more preferably 4 to 15 amino acids. In addition, the linker peptide may be composed of glycine (G), serine (S) or alanine (A), while the sequence of the linker peptide may be preferably an amino acid sequence of $(GA)_n$ or $(GGGGS)_m$, represented by SEQ ID NO: 44, (provided that n and m each are independently an integer of 1 to 20, and mean the number of repetition of the sequence in parentheses), and more preferably an amino acid sequence of GAGA represented by SEQ ID NO: 46 or $(GGGGS)_3$ represented by SEQ ID NO: 45.

In an Example of the present invention, a fusion protein in which a tissue-penetrating peptide (TPP) is fused to a ranibizumab mutant through the linker was constructed, and the effect thereof was investigated. The fusion protein may include a fusion protein (IDB0062) having a form in which TPP #2 is linked to the ranibizumab mutant (IDB0061) according to the present invention by a linker ($(GGGGS)_3$) represented by SEQ ID NO: 45, and consisting of the amino acid sequences represented by SEQ ID NO: 12 and SEQ ID NO: 14; a fusion protein (IDB0064) having a form in which TPP #5 is linked to the ranibizumab mutant (IDB0061) according to the present invention by a linker ($(GGGGS)_3$) represented by SEQ ID NO: 45, and consisting of the amino acid sequences represented by SEQ ID NO: 16 and SEQ ID NO: 18; and a fusion protein (IDB0072) having a form in which TPP #2 is linked to the heavy chain of bevacizumab by a linker ($(GGGGS)_3$) represented by SEQ ID NO: 45, and consisting of the amino acid sequences represented by SEQ ID NO: 20 and SEQ ID NO: 22.

The pharmaceutical composition of the present invention can be used to treat any eye disease by neovascularization.

As used herein, the expression "eye disease by neovascularization" refers to any eye disease by vascular growth or proliferation, vascular leakage, or those associated therewith.

The eye disease by neovascularization may be selected from the group consisting of proliferative vitreoretinopathy, macular degeneration, pigmentary retinopathy, diabetic retinopathy, choroidal neovascularization, neovascular glaucoma, ischemic optic neuropathy, retinopathy of prematurity, retinopathy of immaturity, epidemic conjunctivitis, neovascular iris disease, retrolental fibroplasias, atopic keratitis, superior limbic keratitis, pterygium keratitis sicca, phlyctenular keratoconjunctivitis, scleritis, and diabetic macular edema, and more preferably, examples thereof may be macular degeneration and diabetic macular edema, but are not limited thereto.

In accordance with another aspect of the present invention, there is provided a method for preparing an anti-vascular endothelial growth factor (anti-VEGF) agent with an improved efficacy and ability to overcome resistance, the method comprising: (a) transforming host cells with a recombinant vector, the recombinant vector comprising a nucleic acid sequence encoding a fusion protein in which a tissue-penetrating peptide is fused to an anti-vascular endothelial growth factor (anti-VEGF) agent; (b) culturing the cells; and (c) collecting a fusion protein from the cells.

The nucleic acid sequence encoding the fusion protein may be selected from the group consisting of SEQ ID NO: 13, SEQ ID NO: 15, SEQ ID NO: 17, SEQ ID NO: 19, SEQ ID NO: 21, and SEQ ID NO: 23. Specifically, the nucleic acids encoding the light and heavy chains of the ranibizumab modified form IDB0062 according to the present invention are described by the nucleotide sequences of SEQ ID NO: 13 and SEQ ID NO: 15; the nucleic acids encoding the light and heavy chains of the ranibizumab modified form IDB0064 according to the present invention are described by the nucleotide sequences of SEQ ID NO: 17 and SEQ ID NO: 19; and the nucleic acids encoding the light and heavy chains of the bevacizumab modified form IDB0072 according to the present invention are described by the nucleotide sequences of SEQ ID NO: 21 and SEQ ID NO: 23.

As used herein, the vector refers to an expression vector that is prepared by inserting the polynucleotide of the present invention into a vector by a method well known in the art to express the fusion protein of the present invention using appropriate transcription/translation regulatory sequences.

The polynucleotide sequence cloned according to the present invention may be operably linked to an appropriate expression control sequence, while the operably linked gene sequence and the expression control sequence may be contained in one expression vector having both a selection marker and a replication origin. The term "operably linked" means that the polynucleotide (nucleic acid) sequence is linked in a manner of enabling gene expression by an expression control sequence. The term "expression control sequence" refers to a DNA sequence that controls the expression of an operably linked polynucleotide sequence in a particular host cell. Such an expression control sequence may include at least one selected from the group consisting of a promoter for performing transcription, an operator sequence for controlling transcription, a sequence for encoding a suitable mRNA ribosomal binding site, a sequence for controlling the termination of transcription and translation and the like.

The vector used as a parent vector of the expression vector is not particularly limited, while any plasmid, virus, or other medium, which is commonly employed for expression in a microorganism used as a host cell in a technical field to which the present invention pertains, can be used. Examples of the plasmid may include *Escherichia coli*-derived plasmids (pBR322, pBR325, pUC118, pUC119, and pET-22b (+)), *Bacillus subtilis*-derived plasmids (pUB110 and pTP5), and yeast-derived plasmids (YEp13, YEp24, and YCp50), but are not limited thereto. Examples of the virus may include animal viruses (such as retrovirus, adenovirus, and vaccinia virus), insect viruses (such as baculovirus), and the like, but are not limited thereto.

The host cells may be selected from ones that can control the expression of an inserted sequence or produce a target product from a gene in a preferable specific manner. Different host cells have their own characteristic and specific mechanisms for protein translation, post-translational processing, and transformation. A suitable cell line or host system may be selected from ones that provide preferable transformation and processing of expressed heterologous proteins. The expression in yeasts can produce biologically active products. The expression in eukaryotic cells can increase the likelihood of "natural" folding.

Any host cell known in the art may be used as a host cell as long as it is capable of performing continuous cloning and expressing while stabilizing the vector of the present invention. For example, *E. coli* JM109, *E. coli* BL21DE, *E. coli* DH5, *E. coli* RR1, *E. coli* LE392, *E. coli* B, *E. coli* X 1776, and *E. coli* W3110. Also, *Agrobacterium* spp. strains (such as *Agrobacterium* A4), Bacilli spp. strains (such as *Bacillus subtilis*), other intestinal bacteria such as *Salmonella typhimurium* or *Serratia marcescens*, and various *Pseudomonas* spp. strains may be used as host cells.

In addition, in cases where the vector of the present invention is transfected into eukaryotic cells, yeast (*Saccharomyces cerevisiae*), and insect cells and human cells (e.g., CHO cell line (Chinese hamster ovary), W138, BHK, COS-7, 293, HepG2, 3T3, RIN, and MDCK cell lines) may be used as host cells.

Any known method whereby a vector is delivered into a host cell to transform the host cell may be used, but is not particularly limited. For example, *E. coli* can be transformed by heat shock or electroporation. When a producing cell line is constructed using animal cells, the cells can be transfected by calcium phosphate precipitation, a DEAE-dextran method, electroporation, direct microinjection, a DNA-loaded liposome method, a lipofectamine-DNA complex method, cell sonication, gene bombardment using high-velocity microprojectiles, a polycation method, and receptor-mediated transfection. Some of these techniques may be modified for use in vivo or ex vivo.

Transgenic cells are cultured under appropriate conditions allowing the expression of fusion proteins, while these conditions can be implemented according to methods well known to a person skilled in the art. Transgenic cells may be cultured in large quantities by a routine culturing method. A medium containing carbon sources, nitrogen sources, vitamins, and minerals may be used as a culture medium, of which one example is 2×YT medium. Cells can be cultured under conventional cell culture conditions. For instance, the cells may be cultured at a temperature range of 15-45° C. for 10-40 hours. Centrifugation or filtration may be carried out to remove cells in the culture liquid and collect only the culture medium, and such a step may be carried out as needed by a person skilled in the art. The culture medium (filtrate) with the cells removed is refrigerated by a conventional method, so that the culture medium can be preserved for a short time so as not to lose its activity.

The fusion proteins expressed in transgenic cells (or transformants) can be purified in a conventional manner, and for example, the fusion proteins of the present invention can be purified by using salting out (e.g, ammonium sulfate precipitation or sodium phosphate precipitation), solvent precipitation (e.g., protein fraction precipitation using acetone, ethanol, and the like), dialysis, gel filtration, ion exchange, column chromatography (such as reverse-phase column chromatography, and affinity column chromatography) and ultra-filtration, alone or in combination (Maniatis et al, Molecular Cloning: A Laboratory Manual, Cold Spring Harbor Laboratory, Cold Spring Harbor, N.Y. (1982); Sambrook et al, Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990)).

Advantageous Effects

The pharmaceutical composition comprising, as an active ingredient, a fusion protein in which a tissue-penetrating peptide is fused to an anti-vascular endothelial growth factor (anti-VEGF) agent, of the present invention, increases the tissue penetration of the anti-vascular endothelial growth factor agent and improves the ability of the drug transfer into the choroidal tissues at the time of intraocular injection, thereby allowing its development in the form of eye drops as well as showing effects of treating drug-resistant patients, reducing the dose, and increasing the frequency of administration.

MODE FOR CARRYING OUT THE INVENTION

Hereinafter, the present invention will be described in detail.

However, the following examples are merely for illustrating the present invention and are not intended to limit the scope of the present invention.

Example 1

Construction of Ranibizumab Modified Form Having Fused Tissue-Penetrating Peptide 1-1 Construction of Ranibizumab Mutant IDB0061 with Increased Productivity The low production yield of ranibizumab is due to a low culture yield of Fab fragments and a complicated post-treatment process by the polymorphism of produced proteins through periplasmic expression. To overcome this problem, a particular amino acid sequence of ranibizumab was converted through protein engineering (such as point mutation introduction) so that a producing cell line was optimized so as to export most of the produced proteins out of cells to increase the expression rate and to produce only uniform-shaped proteins, thereby producing ranibizumab mutant IDB0061. Accordingly, it was confirmed that the culture productivity was improved and the purification process was simplified, leading to a remarkable improvement in production yield.

Specifically, according to the protein engineering for conversion of the amino acid sequence of ranibizumab, a gene was synthesized by changing cysteine to serine at the terminus in the nucleotide sequence of ranibizumab. Thereafter, an expression test was conducted after transformation into producing cell line SUPEX5 (KCTC 12657BP).

The construction procedure of a light chain region of ranibizumab mutant IDB0061 is as follows: The nucleic acid sequence of ranibizumab was obtained from the related patent and subjected to codon optimization, on the basis of which a nucleic acid of Fab light chain variable region (VL) comprising a signal sequence was synthesized. The CL region of Fab was constructed by PCR using anti-albumin Fab SL335 vector as a template and primers (SEQ ID NOs: 24 and 25). The construction procedure of a heavy chain region of ranibizumab mutant IDB0061 is as follows: The nucleic acid sequence of ranibizumab was obtained from the related patent and subjected to codon optimization, on the basis of which a nucleic acid of Fab heavy chain variable region (VH) comprising a signal sequence (gIII) was synthesized. The CH1 region of Fab was constructed by PCR using anti-albumin Fab SL335 vector as a primer and primers (SEQ ID NOs: 32 and 33).

TABLE 1

Sequences of primers used for cloning (5' → 3')

| | |
|---|---|
| SEQ ID NO: 24 | tgtggctgcaccatctgtcttcatc |
| SEQ ID NO: 25 | agactctccctgttgaagctctttgtg |
| SEQ ID NO: 26 | cacaaagagcttcaacaggggagagt |
| SEQ ID NO: 27 | ttaacgacgcggacgacctttttgtttt |
| SEQ ID NO: 28 | atgaaaaaaactgcgattgcgattgcggt |
| SEQ ID NO: 29 | gatgaagacagatggtgcagccaca |
| SEQ ID NO: 30 | gggggatccatgaaaaaaactgcgattgcgattgcggt |
| SEQ ID NO: 31 | gggctcgagttaacgacgcggacgacctttttgtttt |
| SEQ ID NO: 32 | gcctccaccaagggcccatc |
| SEQ ID NO: 33 | agaagatttgggctcaactttcttgtccac |
| SEQ ID NO: 34 | gtggacaagaaagttgagcccaaatctt |
| SEQ ID NO: 35 | ttaacgacgcggacgacctttttgtttt |
| SEQ ID NO: 36 | atgaaaaaactgctgttcgcgattccgc |
| SEQ ID NO: 37 | cgatgggcccttggtggagg |
| SEQ ID NO: 38 | ggggaattcatgaaaaaactgctgttcgcgattccgc |
| SEQ ID NO: 39 | gggaagcttttaacgacgcggacgacctttttgtttt |
| SEQ ID NO: 40 | cccggatccatgaaaaaaactgcgattgcgattgcggt |
| SEQ ID NO: 41 | cccgaattcatgaaaaaactgctgttcgcgattccgc |
| SEQ ID NO: 42 | ggctctcacaccccgggtaactctaaaccaacacgcacaccaaggcgttaactcgaggg |

The amino acid sequence of ranibizumab was subjected to point mutation using a method ordinarily used in a field of protein engineering. Specifically, cysteine was substituted with serine at the 214th amino acid residue in the light chain amino acid sequence of ranibizumab, while cysteine was substituted with serine at the 226th amino acid residue in the heavy chain amino acid sequence of ranibizumab. The amino acid sequences of the light chain and the heavy chain of the point-mutated ranibizumab mutant IDB0061 were indicated by SEQ ID NO: 8 and SEQ ID NO: 10, respectively, while the nucleic acid sequences encoding the amino acid sequences were indicated by SEQ ID NO: 9 and SEQ ID NO: 11, respectively.

The sequence of ranibizumab mutant IDB0061 finally completed through PCR was cloned in pHEKA vector, and transformed into SUPEX5 strain. Specifically, after 100 µl of competent cells was added to a 1-mm cuvette, 3 µl of the DNA was added thereto, and then gene introduction was carried out by electric shock at 1800 V, thereby completing the preparation of a producing cell line.

The producing cell lines of ranibizumab and IDB0061 were respectively inoculated at 1% (v/v) in 50 ml of 2×YT media (100 mM potassium phosphate buffer, pH 7.2, 50 µg/ml kanamycin), and pre-cultured at 220 rpm for 18 hours at 28° C. Then, 180 ml of 2×YT media were added in 1 L-baffled flask, and 20 ml of 1 M potassium phosphate (pH 7.2) and 50 µg/ml kanamycin that were previously bacteriostatic were added to the sterilized main culture media, and then the pre-culture liquid was inoculated until $OD_{600}$ was about 0.15. Thereafter, the cells were cultured at 28° C. and 220 rpm until $OD_{600}$ was 0.5-0.7, followed by addition of 0.1 mM IPTG, and then the temperature was lowered to 20° C. to induce expression. After 21 hours of the expression induction, the culture liquid was centrifuged to collect a culture supernatant, which was then filtered by a depth filter and membrane sterile filter, and loaded on a protein L column, thereby purifying target proteins.

As a result of productivity comparison between ranibizumab mutant IDB0061 according to the present invention and original ranibizumab, as shown in Table 2, it was verified that IDB0061 had higher productivity than ranibizumab through only batch culture using basal media, and purification at a purity of 95% or higher could be attained from the culture liquid without cell disruption through a one-step process using an adsorption column, thereby achieving process simplification.

TABLE 2

Comparision of productivity among ranibizumab, ranibizumab mutant and ranibizumab modified form according to the present invention

| Drug name | cultivation | Productivity (mg/L) | Purification | Purity |
|---|---|---|---|---|
| Novartis Ranibizumab | Flask batch culture | <1[1] | Cell extraction & protein G | >98% |
| IDB0061 | | 6~7 | Affinity column | >95%[2] |
| IDB0062 | | 4~5 | (protein L) | >95%[2] |
| IDB0064 | | 3~4 | | >95%[2] |

1. Anti-VEGF antibody patent (PCT/US1998/006604, Genetech)
2. The purity of the final purified product is indicated for Novartis' ranibizumab, whereas the purity of primary purified product through Protein L column is indicated for IDB0061 and IDB0062.

1-2 Fusion of Ranibizumab Mutant and Tissue-Penetrating Peptide

Figure 1B:
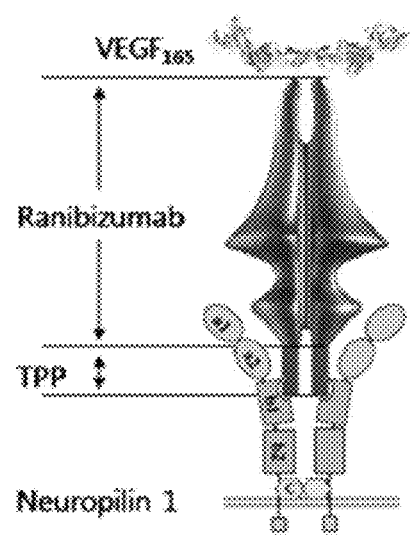
FIG. 1B is a schematic diagram showing the binding of a fusion protein, in which a tissue-penetrating peptide is fused to an anti-vascular endothelial growth factor, to VEGF and neuropilin receptor-1.
Figure 1C:
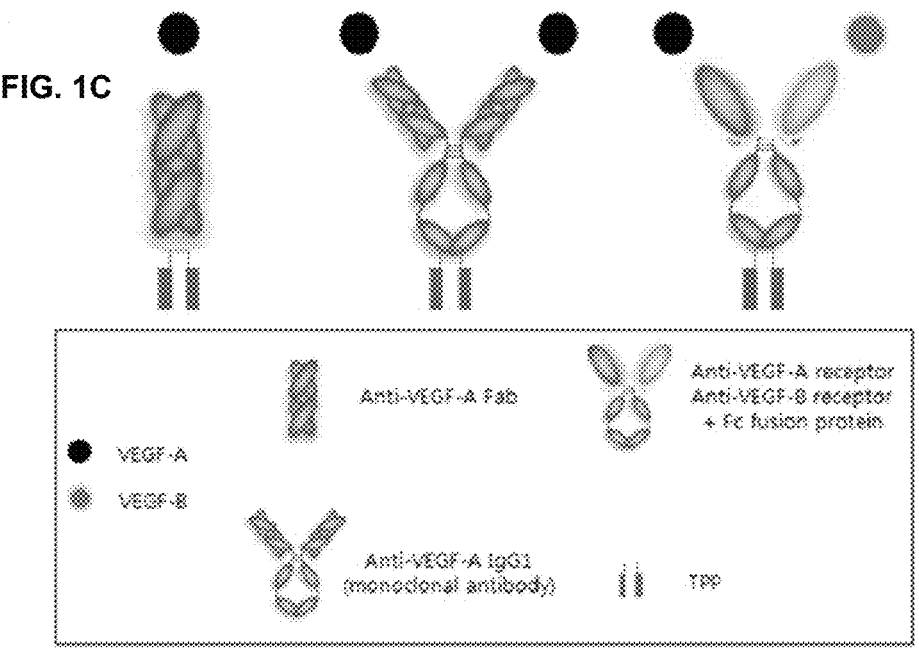
FIG. 1C is a schematic diagram of modified forms in which a tissue-penetrating peptide binds to various vascular endothelial growth factor inhibitor forms (Fab, whole IgG, and Fc fusion protein).

In order to improve an efficacy of and overcome a resistance against ranibizumab as an anti-VEGF agent, the present inventors attempted to fuse a tissue-penetrating peptide (TPP), which is capable of binding to both neuropilin 1 (NRP1) and neuropilin 2 or only neuropilin 1, to the C-terminus of ranibizumab. The amino acid sequences of TPP are shown in Table 3 below. Among the sequence listings in Table 3, TPPs having the amino acid sequences of SEQ ID NOs: 1 to 4 can bind to both neuropilin 1 and 2, whereas TPPs having the amino acid sequence of SEQ ID NOs: 5 to 7 can bind specifically to neuropilin 1. A schematic diagram of a fusion protein in which TPP is fused to ranibizumab is shown in FIG. 1. Specifically, fusion proteins, in which various TPPs (peptides specifically binding to neuropilin receptors) described in Table 3 are fused to the C-terminus of ranibizumab mutant IDB0061 constructed in Example <1-1>, and cell lines producing the fusion proteins were constructed by APRILBIO.

Meanwhile, among TPPs shown in Table 3, TPP #2 having the amino acid sequence of SEQ ID NO: 2 was obtained by modifying the C-terminus regions of $VEGF_{165}$ as an intrinsic ligand of neuropilin and class 3 semaphorin ligands; and TPP #5 was obtained by isolating and identifying a peptide derived from a clone selectively binding to the b1 domain of neuropilin 1 using both b1b2 domain protein of neuropilin 1 and b1b2 domain protein of neuropilin 2 as competitors. Here, AVASTIN was fused thereto using a linker to act as a bivalent in the neuropilin receptor, so that these peptides were designed to have a tissue penetration while having a similar affinity to VEGF and Sema3A ligands.

TABLE 3

| | |
|---|---|
| TPP#1 (SEQ ID NO: 1) | HTPGNSNKWKHLQENKKGRNRR |
| TPP#2 (SEQ ID NO: 2) | HTPGNSNKWKHLQENKKGRPRR |
| TPP#3 (SEQ ID NO: 3) | REAPGAPRSPEPQDQKKPRNRR |
| TPP#4 (SEQ ID NO: 4) | REAPGAPRSPEPQDQKKPRPRR |
| TPP#5 (SEQ ID NO: 5) | HTPGNSKPTRTPRR |
| TPP#6 (SEQ ID NO: 6) | HTPGNSNQFVLTSTRPPR |
| TPP#7 (SEQ ID NO: 7) | HTPGIATRTPR |

The construction procedure of IDB0062 having a form in which TPP #2 peptide is linked to ranibizumab mutant IDB0061 without bound TPP (a form in which only point mutation is introduced into ranibizumab) by a linker is as follows.

Specifically, a light chain region of ranibizumab mutant IDB0062 having fused TPP was constructed by obtaining the nucleic acid sequence of ranibizumab from the related patent, and performing codon optimization, on the basis of which a nucleic acid of a light chain variable region (VL) comprising a signal sequence was synthesized. Then, a nucleic acid (CL'-linker-TPP #2) comprising a linker and the TPP #2 sequence in addition to a partial sequence in which cysteine is substituted with serine in the C-terminus of the light chain constant region (CL) was synthesized. The CL region of Fab was constructed by PCR using anti-albumin Fab SL335 as a template and primers (SEQ ID NOs: 24 and 25), and CL'-linker-TPP #2 was constructed by PCR using the synthesized CL'-linker-TPP #2 nucleic acid as a template and primers (SEQ ID NOs: 26 and 27). These two products were linked through linking PCR to construct the CL-linker-TPP #2 oligonucleotide. VL was constructed using the synthesized VL nucleic acid as a template and primers (SEQ ID NOs: 28 and 29), and then assembly PCR was conducted using primers (SEQ ID NOs: 30 and 31, including BamHI and XhoI sequences) together with CL-linker-TPP #2 to complete the final VL-CL-linker-TPP #2 sequence.

A heavy chain region of ranibizumab mutant IDB0062 having fused TPP #2 was constructed by obtaining the nucleic acid sequence of ranibizumab from the related patent, and performing codon optimization, on the basis of which a nucleic acid of a heavy chain variable region (VH) comprising a signal sequence (gIII) was synthesized. Then, a nucleic acid (CH1'-linker-TPP #2) comprising a linker and the TPP #2 sequence in addition to a partial sequence in which cysteine is substituted with serine in the C-terminus of the heavy chain constant region (CH1) was synthesized. The CH1 region of Fab was constructed by PCR using anti-albumin Fab SL335 as a template and primers (SEQ ID NOs: 32 and 33), and CH1'-linker-TPP #2 was constructed by PCR using the synthesized CH1'-linker-TPP nucleic acid as a template and primers (SEQ ID NOs: 34 and 35). These two products were linked through linking PCR to construct the CH1-linker-TPP #2 oligonucleotide. VH was constructed using the synthesized VH nucleic acid as a template and primers (SEQ ID NOs: 36 and 37), and then assembly PCR was conducted using primers (SEQ ID NOs: 38 and 39, including EcoRI and HindIII sequences) together with CL-linker-TPP #2 to complete the final VH-CH1-linker-TPP #2 sequence. The light chain of the fragment finally completed through PCR was digested with BamHI and XhoI, and the heavy chain thereof was digested with EcoRI and HindIII, and these were cloned into pHEKA vector digested with the same restriction enzymes. The pHEKA vector comprising the IDB0062 sequence, which was completed by the foregoing method, was transformed into SUPEX5 strain. Specifically, after 100 µl of competent cells was added to a 1-mm cuvette, 3 µl of the DNA was added thereto, and then gene introduction was carried out by electric shock at 1800 V, thereby completing the preparation of a producing cell line.

The amino acid sequences of the light chain and the heavy chain of the constructed IDB0062 were indicated by SEQ ID NO: 12 and SEQ ID NO: 13, respectively, while the nucleic acid sequences encoding the amino acid sequences were indicated by SEQ ID NO: 13 and SEQ ID NO: 15, respectively 1-3 Selection of Ranibizumab Modified Form IDB0062

The affinity to a neuropilin receptor and the tight junction disruption ability between endothelial cells were compared for various ranibizumab modified form candidate proteins constructed in Example 1-2.

First, the affinity to a neuropilin receptor was performed on neuropilin 1 (NRP 1). Specifically, surface plasmon resonance (SPR) was performed using Biacore 2000 (GE Healthcare) in order to investigate the binding ability of TPP to the neuropilin 1 domain. Specifically, each neuropilin 1 domain was diluted in 10 mM Na-acetate buffer (pH 4.0), and fixed on CM5 sensor chip (GE Healthcare, USA) at about 1,000 response units (RU). HBS-EP buffer (10 mM HEPES, 2 mM ethylenediaminetetraacetic acid, and 0.005% surfactant P20, pH 7.4, GE Healthcare) at a flow rate of 30 µl/min was used for analysis, while VEGF165 was used for analysis at concentrations from 80 nM to 5 nM, semaphorin 3A from 1 uM to 62.5 nM, and TPP from 25 uM to 1.5625 uM. After the association/dissociation analysis, the CM5 chip was regenerated by allowing buffer (20 mM NaOH, 1M NaCl, pH 10.0) to flow at a flow rate of 30 µl/min for 1 minute. Sensorgrams obtained from association for 3 minutes and dissociation for 3 minutes were subjected to normalization and subtraction in comparison with blank cells to calculate affinity.

In addition, the disruption ability of tight junction between endothelial cells was evaluated by measuring the degree of inhibition of VE-cadherin and E-cadherin by the proteins. It has been known that the reduction in expression of VE-cadherin and E-cadherin in endothelial cells results in the disruption of tight junction between endothelial cells, and as a result, the delivery power (or tissue penetrating power) of a drug into the choroidal tissue is increased upon the intraocular administration of the drug. Specifically, for an experimental method for indirectly confirming the enhancement of vascular penetration of TPP, the change of VE-cadherin was investigated by Western blot. Specifically, for confirmation of the enhancement of vascular penetration, HUVEC cells were seeded at a density of 3×10⁵ cells/well in a 6-well plate, cultured for 24 hours, and treated with 1 µM TPP for 10 minutes, followed by Western blot. The gels subjected to SDS-PAGE were transferred to PVDF membranes, and detection was carried out using primary antibodies (SantaCruz) recognizing VE-cadherin and β-actin and HRC-conjugated secondary antibodies (SantaCruz). Analysis was performed using ImageQuant LAS4000 mini (GE Healthcare).

The experimental results, as shown in Table 4, confirmed that TPP #2-fused Fc (Fc-TPP #2) bound to a neuropilin receptor (NRP 1) at a high level (similar level to Sema3A ligand), and remarkably inhibited VE-cadherin. TPP #5-fused Fc (Fc-TPP #5) was shown to have higher binding ability to NRP 1 than Sema3A and also have more excellent inhibitory effect on VE-cadherin. It was confirmed that IDB0062 binds to the neuropilin receptor (NRP 1) at a high level, and inhibits VE-cadherin at a similar level to Fc-TPP #2.

TABLE 4

TPP candidate selection

| Clone | Linker length/ TPP length (number of amino acids) | Receptor (neuropilin) | Affinity, $K_D(M)$ | VE-cadherin inhibition |
|---|---|---|---|---|
| VEGF₁₆₅ | — | NRP 1 | $3.51 \pm 0.36 \times 10^{-9}$ | ++ |
| Sema3A | — | NRP 1 | $2.79 \pm 0.14 \times 10^{-8}$ | + |
| Fc-TPP#2 | 15/22 | NRP 1 | $6.3 \pm 0.21 \times 10^{-8}$ | ++ |
| Fc-TPP#5 | 15/14 | NRP 1 | $1.7 \pm 0.2 \times 10^{-9}$ | +++ |
| IDB0062 | 15/22 | NRP 1 | $1.0 \pm 0.11 \times 10^{-8}$ | ++ |

1-4 Confirmation of Productivity of Ranibizumab Modified Form IDB0062

The productivity of IDB0062 was investigated by the same method as in Example 1-1. As shown in Table 1, the results confirmed that IDB0062 in which TPP #2 was fused to IDB0061 also showed about 5 times or higher productivity than ranibizumab.

In addition, the purity of the first purified product obtained by an adsorption column was analyzed by HPLC. HPLC analysis was carried out in the following manner. The first purified product obtained by an adsorption column was concentrated using Amicon (Millipore, 10K), and then diluted to a final concentration of 0.5 mg/ml by exchange with a formulation buffer (10 mM histidine, 0.1% Tween20, 10% trehalose). Waters Alliance e2695 was used as an analytical instrument, BioSuite 250 UHR SEC (4.6×300 mm, 4 um, Waters) as a column, and 20 mM potassium phosphate buffer (250 mM KCl, pH 6.2) as a mobile phase. For the analysis, 20 µl of the concentrated sample was injected, and analyzed at a flow rate of 0.35 ml/min for 20 minutes. Protein peaks were analyzed at a UV 280 nm wavelength.

The experimental results confirmed that ranibizumab is a mixture of three main components, of which only the third component is an active ingredient, whereas IDB0062 was produced in a single form (FIG. 2).

1-5 Construction of Ranibizumab Modified Form IDB0064 and Confirmation of Productivity Thereof Following ranibizumab modified form IDB0062, ranibizumab modified form IDB0064 was constructed by linking and fusing TPP #5, of which the VE-cadherin inhibitory effect was confirmed in Example <1-3>, thereto using a linker and then productivity thereof was investigated.

The detailed construction procedures of IDB0064 are as follows. For binding of TPP #5 as new TPP to IDB0061, gene cloning was carried out. In order to use IDB0062 as a template and replace the TPP of the C-terminus from TPP #2 to TPP #5, specific primers (SEQ ID NOs: 40, 41 and 42) were used. The primers were prepared by setting an annealing region in the anterior sequences of a part shared by TPP #2 and TPP #5 and then extending the sequences of TPP #5 therefrom, and cloning was carried out using the primers. PCR was performed for 30 cycles in the order of denaturation (95° C., 40 sec), annealing (65° C., 40 sec), extension (72° C., 1 min) to obtain Fab light chain-TPP #5 and Fab heavy chain-TPP #5 genes. The light chain of the PCR product was treated with BamHI and XhoI, while the heavy chain was treated with EcoRI and HindIII, followed by being ligated to pHEKA vector which was then transformed into the producing cell line SUPEX5.

The amino acid sequences of the light chain and the heavy chain of the constructed IDB0064 were indicated by SEQ ID NO: 16 and SEQ ID NO: 18, respectively, while the nucleic acid sequences encoding the amino acid sequences were indicated by SEQ ID NO: 17 and SEQ ID NO: 19, respectively.

Figure 3:
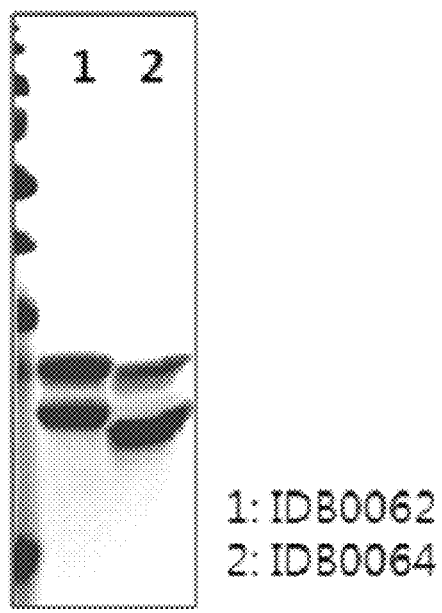
FIG. 3 shows the 12% non-reducing SDS-PAGE gel analysis results of primary purified products of the fusion proteins according to the present invention (IDB0062: Fab fusion protein in which tissue-penetrating peptide TPP #2 is fused to a ranibizumab mutant; IDB0064: Fab fusion protein in which tissue-penetrating peptide TPP #5 is fused to a ranibizumab mutant).

The productivity of the constructed IDB0064 in the producing cell line was investigated. The IDB0064 producing cell line was inoculated at 1% (v/v) in 50 ml of 2×YT media (100 mM potassium phosphate buffer, pH 7.2, 50 µg/ml kanamycin), and pre-cultured at 220 rpm for 18 hours at 28° C. Then, 180 ml of 2×YT media were added in 1 L-baffled flask, and 20 ml of 1 M potassium phosphate (pH 6.4) and 50 µg/ml kanamycin that were previously bacteriostatic were added to sterilized main culture media, and then the pre-culture liquid was inoculated such that OD₆₀₀ was about 0.15. Thereafter, the cells were cultured at 28° C. and 220 rpm until OD₆₀₀ was 0.5-0.7, followed by addition of 0.05 mM IPTG, and then the temperature was lowered to 20° C. to induce expression. After 21 hours of the expression induction, the culture liquid was centrifuged to collect a culture supernatant, which was then filtered by a depth filter and membrane sterile filter, and loaded on a protein L column, thereby purifying target proteins. As shown in Table 2 and FIG. 3, the purification results confirmed that even the linkage of the TPP #5 sequence constructed as an artificial nucleotide sequence to IDB0061 Fab favorably induced expression, so that a target protein with relatively high purity could be obtained at a productivity of about 3-4 mg/L through only primary purification.

Example 2

Confirmation of Bivalent Characteristics of Ranibizumab Modified Form IDB0062

The binding ability of ranibizumab modified form IDB0062 to VEGF-A and neuropilin 1 receptor was investigated.

2-1 SPR (Biacore2000) Assay of Binding Ability to Neuropilin 1 Receptor

For investigation of the binding ability of IDB0062 and IDB0072 to NRP1, SPR assay was performed. After the Biacore CM5 chip was activated with EDC/NHS mixture, target protein NRP1 was diluted in a fixing buffer (10 mM sodium acetate, pH 5.5), and fixed to final 79 Ru through calculation at Rmax: 200. IDB0062 and IDB0072 samples were then diluted up to 12.5 nM to 400 nM in HBSEP buffer before the assay. The analytical flow rate was 30 µl/min, and as a result, sensorgrams were obtained based on the result graphs to calculate Kd values.

As shown in Table 4, the binding ability of IDB0062 to neuropilin 1 receptor was confirmed to be maintained at a similar level to the binding activity of a control drug (Fc-TPP #2). These results indicate that TPP #2 peptide fused to the C-terminus of ranibizumab favorably binds to neuropilin 1 receptor.

2-2 ELISA Assay of Binding Ability to Neuropilin 1 Receptor

NRP1 (self-produced) was diluted in carbonate coating buffer (0.1 M NaHCO$_3$, pH 9.6) to a final concentration of 10 μg/ml, and the diluted NRP1 was added at 100 μl/well in an ELISA plate (SPL, Immunoplate Maxi binding), followed by coating at 37° C. for 2 hours. Then, the plate was washed three times, blocked (4% skim milk, pH 7.4) at 37° C. for 1 hour, and washed three times. Then, each sample was diluted at appropriate folds, and was used to treat at 100 μl/well, followed by reaction at 37° C. for 1 hour. Upon completion of the sample reaction, the plate was washed three times, and then Goat anti-human kappa light chain Ab-HRP (Sigma Aldrich, A7164) was diluted 5,000 times in blocking buffer, and was used to treat at 100 μl/well, followed by reaction at 37° C. for 1 hour. The plate was washed five times, and treated with TMB substrate (Bethyl, E102) at 100 μl/well, followed by reaction for 2-3 minutes. Thereafter, the reaction was stopped with stop solution (1N HCl) at 100 μl/well and the absorbance at 450 nm was measured using ELISA plate reader.

Figure 4A:
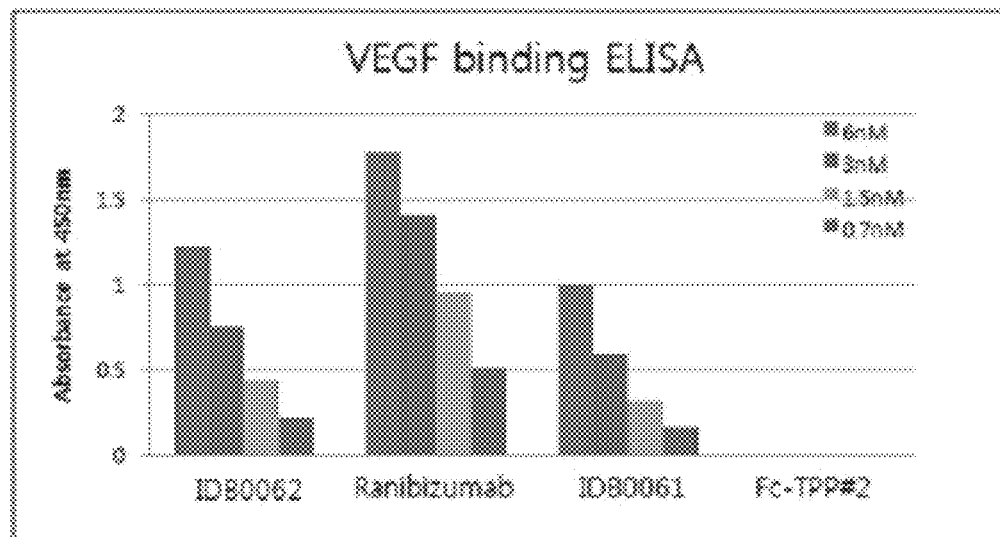
FIG. 4A shows the VEGF binding affinity analysis results of ranibizumab, a ranibizumab mutant, and a fusion protein according to the present invention.
Figure 4B:
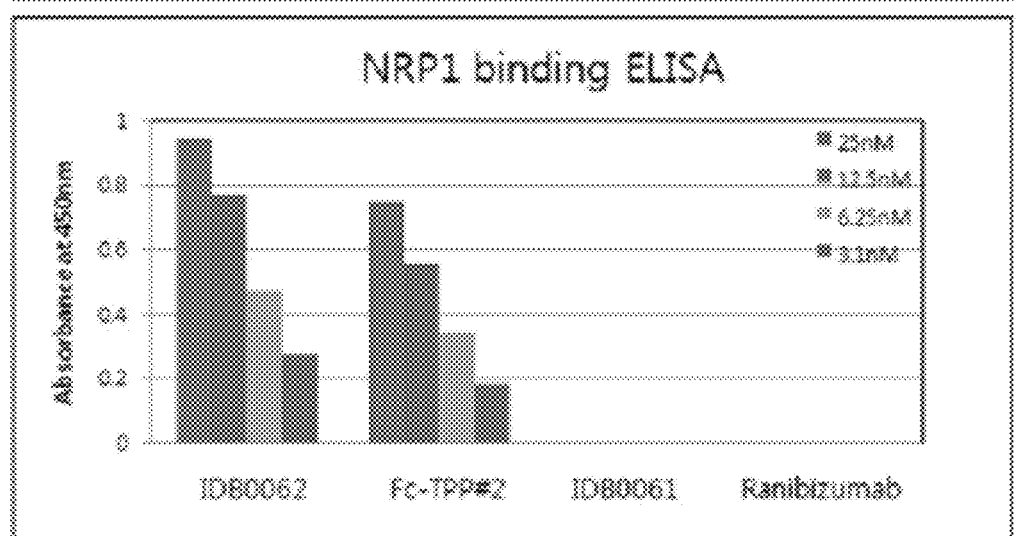
FIG. 4B shows the neuropilin receptor-1 binding ability analysis evaluation results of a tissue-penetrating peptide and a fusion protein according to the present invention (IDB0061: ranibizumab mutant; IDB0062: Fab fusion protein in which tissue-penetrating peptide TPP #2 is fused to a ranibizumab mutant; Fc-TPP #2: Fc fusion protein in which a tissue-penetrating peptide TPP #2 is fused to the Fc-terminus of IgG1).

The ELISA assay also confirmed that the binding ability of IDB0062 to neuropilin 1 receptor was equivalent to that of the control drug (Fc-TPP #2) (FIG. 4B). Therefore, it was again confirmed that the characteristics of TPP #2 peptide were maintained when fused to the C-terminus of ranibizumab.

2-3 ELISA Assay of Binding Ability to VEGF

VEGF (R&D system, 293-VE-500/CF) was diluted in the carbonate coating buffer (0.1 M NaHCO$_3$, pH 9.6) to a final concentration of 3 μg/ml, and the diluted VEGF was added at 100 μl/well in an ELISA plate (SPL, Immunoplate Maxi binding), followed by coating at 37° C. for 2 hours. Then, the plate was washed three times, blocked (4% skim milk, pH 7.4) at 37° C. for 1 hour, and washed three times, and then each sample was diluted to appropriate folds, and was used to treat at 100 μl/well, followed by 37° C. for 1 hour. Upon completion of the sample reaction, the plate was washed three times, and then Goat anti-human kappa light chain Ab-HRP (Sigma Aldrich, A7164) was diluted 5,000 times in blocking buffer, and was used to treat at 100 μl/well, followed by 37° C. for 30 minutes. The plate was washed seven times, and treated with TMB substrate (Bethyl, E102) at 100 μl/well, followed by reaction for 2-3 minutes. Thereafter, the reaction was stopped with stop solution (1N HCl) at 100 μl/well and the absorbance at 450 nm was measured using ELISA plate reader.

As shown in FIG. 4A, the ELISA assay results of IDB0062 confirmed that the binding ability of IDB0062 to VEGF-A was somewhat reduced compared with ranibizumab. The presumed reason is that the complementary-determining region (CDR) binding to VEGF-A is partially changed as the tertiary structure of IDB0062 was changed by an alteration of a specific amino acid on the sequence. However, since the binding ability of ranibizumab is significantly higher than general antibodies, it is considered that such a reduction in binding ability will not cause a substantial deterioration in its clinical efficacy.

Example 3

Evaluation of Stability of Ranibizumab Modified Form IDB0062

It has been confirmed that the alteration of a specific amino acid on the sequence of IDB0062 caused its structural modification and thus the binding ability of IDB0062 to VEGF-A was somewhat reduced compared with ranibizumab. Therefore, in order to investigate how the alteration affects the stability of IDB0062, its stability according to the storage condition and repeated freezing/thawing was analyzed.

The first purified product, after being changed into a formulation buffer, was concentrated to a concentration (5 mg/ml) used in an animal experiment, and then the stability experiment was carried out. For the stability experiment according to the storage condition, the sample was dispensed in 10 μl aliquots, and while being stored at 4° C. and −80° C. for 5 weeks, the sample was taken out on a weekly basis, thawed in ice, and analyzed by VEGF binding ELISA assay. While the procedure in which the sample was frozen at −80° C. and thawed in ice was repeated five times, a partial sample was taken out and evaluated for repeated freezing/thawing stability through VEGF binding ELISA assay.

Figure 5A:
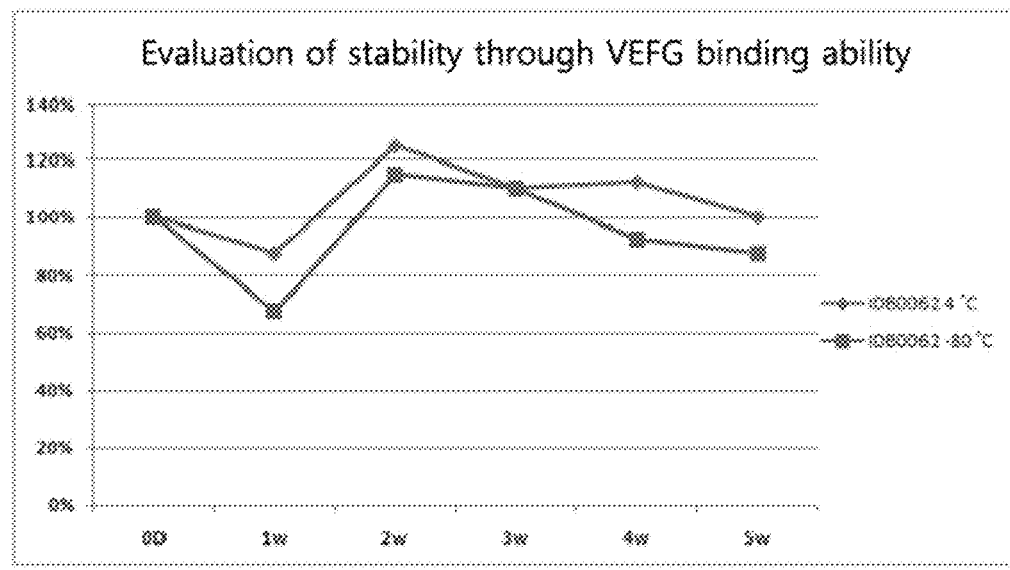
FIG. 5A shows the evaluation results of stability by storage condition of a fusion protein according to the present invention.
Figure 5B:
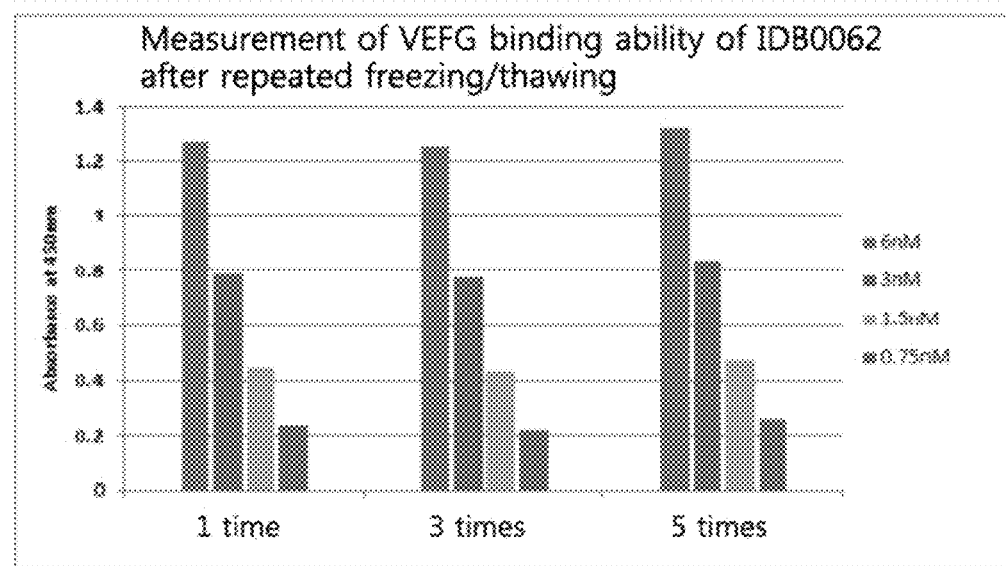
FIG. 5B shows the evaluation results of stability by repeated freezing/thawing of the fusion protein.

As a result, as shown in FIG. 5, the binding ability of IDB0062 to VEGF-A was stably maintained at 4° C. and −80° C. until five weeks after storage, and even physical impact through five times of repeated freezing/thawing did not affect its activity, and thus, it was determined that there was no deterioration in its stability due to an alteration of the amino acid sequence.

Example 4

Evaluation of Ocular Tissue Penetration of Anti-VEGF Agent Modified Form

For analysis of ocular penetration of a ranibizumab modified form, an ex-vivo ocular penetration model was constructed and its efficacy was evaluated. In addition, in order to evaluate whether the tissue penetration was improved by the fusion of a tissue-penetrating peptide in an antibody with a large molecular weight and a more complicated tertiary structure (including Fc fusion protein), the ocular penetration of bevacizumab and its modified form IDB0072 was analyzed at the same time.

4-1 Evaluation of Tissue Penetration of Ranibizumab Modified Form IDB0062

In order to investigate whether TPP fused to the C-terminus of IDB0062 can actually improve tissue penetration through the binding to a neuropilin receptor distributed widely in the ocular endothelial cells; the extracted eyeballs were immersed in FITC-conjugated ranibizumab and IDB0062 solutions to compare the degree of penetration over time therebetween.

In order to increase conjugation efficiency of protein and FITC, a protein sample was adjusted to a concentration of 1 mg/ml through an exchange with 100 mM sodium carbonate buffer (pH 9.0), and mixed with FITC (1 mg/ml in DMSO), followed by reaction at room temperature for 2 hours. Since TPP #2 peptide has many free amine groups capable of binding FITC, different moles of FITC per protein were applied for the reaction. Thereafter, while unconjugated FITC was removed using PD-10 desalting column, the buffer was changed with PBS, and then the purified product was quantified, and used as a sample for efficacy evaluation. The conjugation results confirmed that the F/P ratios of ranibizumab and IDB0062 were 1.127 and 1.133, respectively, which indicates that almost the same number of moles of FITC bound to one molecule of protein. After the solutions of FITC-conjugated ranibizumab and IDB0062 were diluted to 0.3 mg/ml with PBS, C57BL/6 mouse eyeballs were extracted, immersed therein at 37° C. for 1 hour and 2 hours, and washed with PBS two times for 10 minutes each time, and then paraffin slides were prepared. The eyeballs were fixed at 4° C. for 4 hours using Davidson's solution (glacial acetic acid:ethyl alcohol:neutralized formalin:distilled water=1:3:2:3), and then the anterior tissue of the conjunctiva was partially cut with scissors, and the retinal metaplasia was minimized in a paraffin slide preparation step. After overnight fixation at 4° C. using 10% (v/v) formalin solution, moisture was removed from the tissues by increasing the concentration of alcohol from low to high concentration using an automatic infiltration machine, followed by transparency with xylene and then paraffin penetration. The paraffin penetration-completed tissue was placed in a base mold to make a paraffin block, and 4 sections were prepared using a microtome. The paraffin sections were unfolded to be attached to slides pre-coated with albumin, poly-L-lysine, and saline in a floating constant-temperature water bath. The tissue slides were deparaffinized and then directly mounted, and then FITC was observed using a confocal microscope to investigate the ocular tissue penetration and distribution.

Figure 8A:
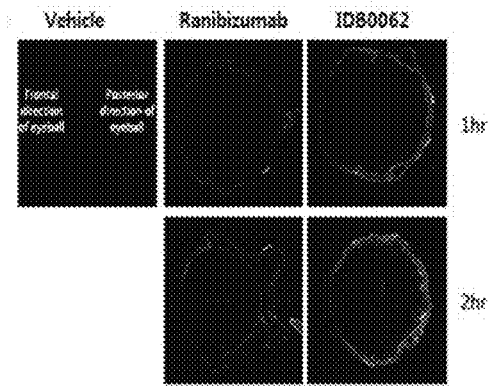
FIG. 8A shows the optical microscopic evaluation results of ocular penetration of ranibizumab modified form IDB0062, which is a fusion protein according to the present invention.
Figure 8B:
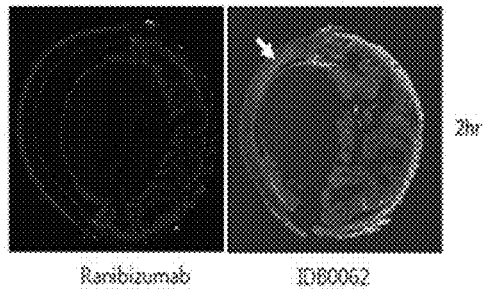
FIG. 8B is a graph obtained by quantifying the results of FIG. 8A.
Figure 8C:
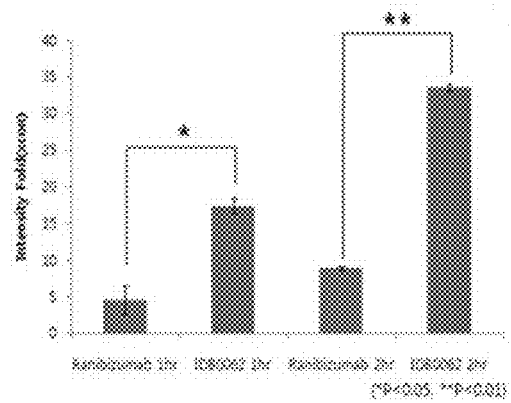
FIG. 8C shows the analysis results of distribution of FITC-conjugated protein in the ocular tissue section after reaction for 2 hours using a fluorescent microscope together with DAPI staining.
Figure 8D:
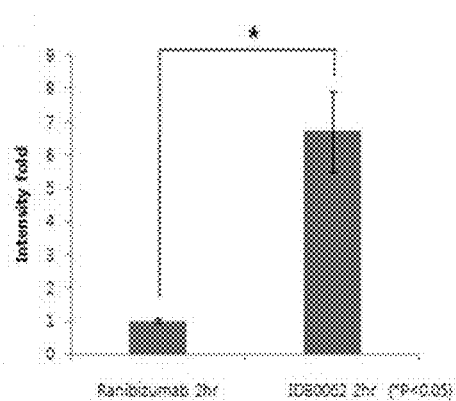
FIG. 8D is a graph obtained by quantifying the results of FIG. 8C.
Figure 8E:
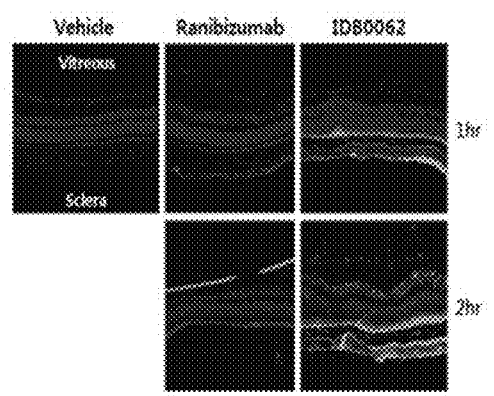
FIG. 8E shows the analysis result of distribution of IDB0062 according to retinal penetration ability thereof by analyzing the retina tissue fragment through a confocal microscope.

As shown in FIGS. 8A and 8B, it was confirmed that IDB0062 began to penetrate into the eyeball rapidly through the cornea and posterior eyeball from 1 hour after the experiment, and within 2 hours, the distribution amounts in the ocular tissue and vitreous body were significantly increased by about four times compared with ranibizumab as a control drug. While the ocular tissue can be clearly distinguished and analyzed through DAPI staining, it was confirmed that, unlike ranibizumab, IDB0062 was distributed in large quantity even inside of the cornea (FIG. 8C, white arrow), and the drug IDB0062 distribution in the eye was increased by about 10 times compared with ranibizumab (FIG. 8D). While the data of FIG. 8E shows a cross-section of the ocular retinal tissue, it was confirmed that the control drug ranibizumab was mostly present near the sclera, whereas IDB0062 has reached the retina through the retina pigment epithelial cell (RPE) layer. In conclusion, the linkage of a tissue-penetrating peptide to ranibizumab which has a poor intraocular tissue penetration ratio could increase the ocular penetration ratio of ranibizumab by about 4 times. It was verified that such a linkage leads to the possibilities of controlling the drug dose, increasing in the interval of drug administration, and being developed as eye drops through the improvement of dosage form, through the improvement of drug penetration.

4-2 Evaluation of Tissue Penetration of Bevacizumab Modified Form IDB0072

The whole antibody proteins, such as bevacizumab, have higher molecular weights and complex tertiary structures, compared with antibody fragments (Fabs), and thus, have unfavorable characteristics in view of tissue penetration. Despite this, in order to investigate whether the fusion of a tissue-penetrating peptide to the C-terminus of bevacizumab overcame these physical limitations and improved its penetration, compared with control drug bevacizumab, the same experiment was conducted.

The construction procedures of bevacizumab modified form IDB0072 are as follows. IDB0072 is a type of antibody fusion protein in which TPP is fused to the C-terminus of bevacizumab by a linker, while the amino acid sequence of TPP is as shown in Table 3 above. Among the sequence listings in Table 3, TPPs having the amino acid sequences of SEQ ID NOs: 1 to 4 can bind to both neuropilin 1 and 2, and TPPs having the amino acid sequence of SEQ ID NOs: 5 to 7 can bind specifically to neuropilin 1. Meanwhile, among TPPs shown in Table 3, TPP #2 was obtained by modifying the C-terminus regions of VEGF165 as an intrinsic ligand of neuropilin and the class 3 semaphorin ligand; and TPP #5 was obtained by isolating and identifying a peptide derived from a clone selectively binding to b1b2 domain of neuropilin 1. Among these TPPs, TPP #2 was fused to bevacizumab using a linker to act as a bivalent against the neuropilin receptor, so that IDB0072 was designed to have tissue penetration while having similar affinity to VEGF and Sema3A.

Specifically, a cell line producing IDB0072 in which TPP #2 having the amino acid sequence of SEQ ID NO: 2 was fused to the C-terminus of bevacizumab was constructed. IDB0072 was cloned into pcDNA3.4 vector. The amino acid sequences of the light chain and the heavy chain of the constructed IDB0072 were indicated by SEQ ID NO: 20 and SEQ ID NO: 22, respectively, while the nucleic acid sequences encoding the amino acid sequences were indicated by SEQ ID NO: 21 and SEQ ID NO: 23, respectively A plasmid encoding a protein in which the NRP1 binding peptide was fused to the constructed antibody heavy chain constant region and a plasmid encoding a light chain protein were transfected into CHO DG44 cells using Neon™ electrophoresis, and then the cells were seeded at $3 \times 10^6$ cells in T25 flask, and cultured at 37° C. Stable cells were secured using a selective marker, and then cultured in a floating state for 7 days under conditions of 100 rpm, 37° C., pH 7.2, 50% $DO_2$ using serum-free SFM4CHO (Hyclone) in a bioreactor. The supernatant was separated from the cells by centrifugation, and sterilized by the 0.22 filter.

The culture liquid of IDB0072 was collected, and each protein was purified with reference to a standard protocol. The culture liquid was subjected to a protein A column (MabselectSure resin, GE healthcare), followed by washing with PBS (pH 7.4). The antibody was eluted at pH 3.0 using 0.1 M glycine buffer, and then the sample was neutralized to pH 7.0 using 1 M Tris buffer. The eluted antibody fractions were concentrated using a MILLIPORE Amicon Ultra (30 MWCO) centrifugal concentrator, followed by exchange with PBS (pH 7.4) buffer. The purified fusion protein in which a peptide specifically binding to selected NRP1 was fused to the antibody heavy chain constant region was quantified using absorbance and absorption coefficient at a corrected wavelength of 280 nm.

In order to increase conjugation efficiency of protein and FITC, bevacizumab and IDB0072 were adjusted to a concentration of 3 mg/ml after an exchange with 100 mM sodium carbonate buffer (pH 9.0), and mixed with FITC (1 mg/ml in DMSO), followed by reaction at room temperature for 2 hours. In order to reduce the conjugation difference by TPP #2 fusion, the mole number of FITC per protein for IDB0072 was differently applied for the reaction, unlike that for control drug bevacizumab. Thereafter, while unconjugated FITC was removed using PD-10 desalting column, the buffer was changed with PBS, and then the purified product was quantified, and used as a sample for efficacy evaluation. The conjugation results confirmed that the F/P ratios of bevacizumab and IDB0072 were 2.18 and 1.98, respectively, which indicates that almost the same number of moles of FITC was bound to one molecule of protein. After the solutions of FITC-conjugated bevacizumab and IDB0072 were diluted to 0.9 mg/ml with PBS, C57BL/6 mouse eyeballs were extracted, immersed therein at 37° C. for 1 hour and 2 hours, and washed with PBS five times for 10 minutes each time, and then paraffin slides were prepared. The subsequent procedures were carried out in the same manner as in Example <4-1>.

In order to evaluate the activity of bevacizumab modified form IDB0072 as prepared, the binding ability of IDB0072 to the neuropilin 1 receptor was investigated by SPR assay. As shown in Table 5, the binding ability of IDB0062 to neuropilin 1 receptor was confirmed to show a similar level, compared with the control drug (Fc-TPP #2) and ranibizumab modified form IDB0062. These results indicate that TPP #2 peptide fused to the C-terminus of bevacizumab favorably binds to the neuropilin 1 receptor.

TABLE 5

Evaluation on activity of TPP-fused form against NRP1

| Clone | Linker length/ TPP length (number of amino acids) | Receptor (neuropilin) | Affinity, $K_D(M)$ | VE-cadherin inhibition |
|---|---|---|---|---|
| Fc-TPP#2 | 15/22 | NRP 1 | $6.3 \pm 0.21 \times 10^{-8}$ | ++ |
| IDB0062 | 15/22 | NRP 1 | $1.0 \pm 0.11 \times 10^{-8}$ | ++ |
| IDB0072 | 15/22 | NRP 1 | $3.1 \pm 0.15 \times 10^{-8}$ | ++ |

Figure 9A:
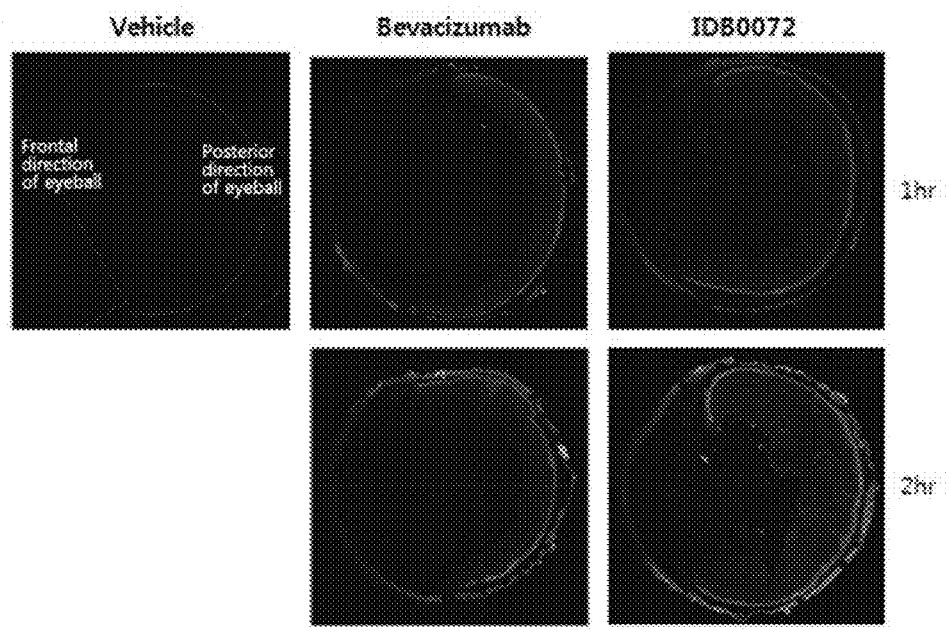
FIG. 9A shows the evaluation results of ocular penetration ability of bevacizumab modified form IDB0072, which is a fusion protein according to the present invention, using a fluorescent microscope.
Figure 9B:
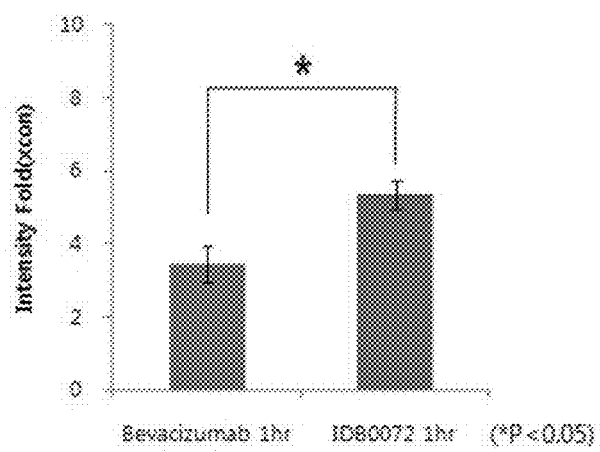
FIG. 9B is a graph obtained by quantifying the results of FIG. 9A.

As shown in FIG. 9A, it was confirmed that IDB0072 also improved ocular penetration, compared with the control drug bevacizumab. It was confirmed that the intraocular distribution of IDB0072 was significantly increased by about 1.5 times, compared with that of bevacizumab at 1 hour and 2 hours (FIG. 9B). It was also confirmed that in spite of its large molecular weight and structure, IDB0072 diffused into the cornea through the conjunctiva, compared with bevacizumab. Therefore, it was verified that even an antibody having a high molecular weight and a complex structure can significantly increase its tissue penetration by linking a tissue-penetrating peptide to the Fc C-terminus. These results indicate that various Fc fusion proteins including antibody proteins can also improve the ocular tissue penetration through the linkage to a tissue-penetrating peptide.

Example 5

Evaluation of Efficacy of Ranibizumab Modified Form Using Corneal Neovascularization Models For evaluation of efficacy of IDB0062, corneal neovascularization models were constructed. Being divided into prevention models and resistance models, they were then used to compare the inhibition of vascularization and the reduction of neovessels between IDB0062 and ranibizumab.

5-1 Prevention Models

For comparison of neovascularization inhibitory effect between IDB0062 and ranibizumab, corneal neovascularization models induced by an alkaline burn were constructed as follows: Cellulose filter paper was cut into a circle with a diameter of 2 mm, and then immersed in a 1M NaOH solution. The 6-week old female C57BL/6 mice were used. After anesthesia (Zoletil 40 mg/kg+Rompun 5 mg/kg, IP), the NaOH filter paper was placed on the left eye cornea to induce an alkaline burn for 30 seconds, followed by sufficient washing with 40 ml of PBS, thereby constructing corneal neovascularization animal models. As for the prevention models, drug treatment was carried out on the same day at which the alkaline burn was induced. Each drug was administered through eye drops at a concentration of 5 mg/ml with 5 μl each time, four times a day for 5 days. After the completion of the administration, the eyeballs were extracted, immersed and fixed in 4% paraformaldehyde solution for one hour, and washed with PBS, and then the cornea was isolated using a dissecting microscope. The isolated cornea was additionally fixed in a 4% paraformaldehyde solution for 12 hours. The fixed cornea was washed with PBS, and subjected to reaction in a blocking buffer (PBS, 0.3% BSA, 0.1% Triton X100) at room temperature for 2 hours. A primary antibody (BD Pharmingen) specific to PECAM-1 (CD31) as a vascular endothelial marker and a primary antibody (Millipore) specific to NG-2 as a pericyte marker were reacted overnight in a refrigerator, and secondary fluorescent antibodies (Alexa Fluor488, Alexa Fluor594, Life Technologies) were reacted at room temperature for 4 hours for tissue staining. Upon completion of the staining procedures, the cornea was transferred to a slide, and mounted on the slide while four cut lines were incised in four directions toward the center of the cornea using a dissecting microscope. Upon completion of the mounting procedures, the cornea slide was observed for aspects of vessels and pericytes by fluorescence microscopy/confocal microscopy.

Figure 6A:
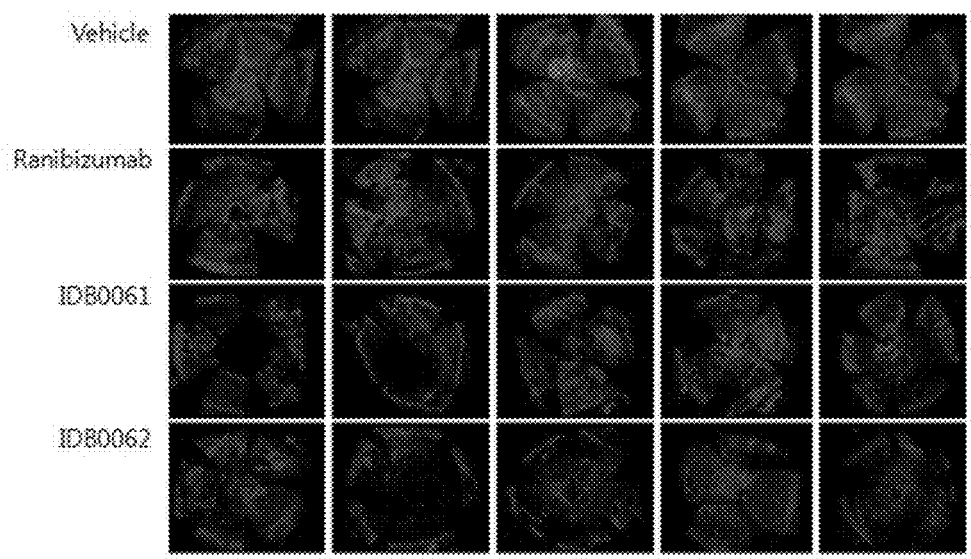
FIG. 6A shows the evaluation results of vascularization inhibitory effect of ranibizumab, a ranibizumab mutant, and a fusion protein according to the present invention in corneal neovascularization prevention models.
Figure 6B:
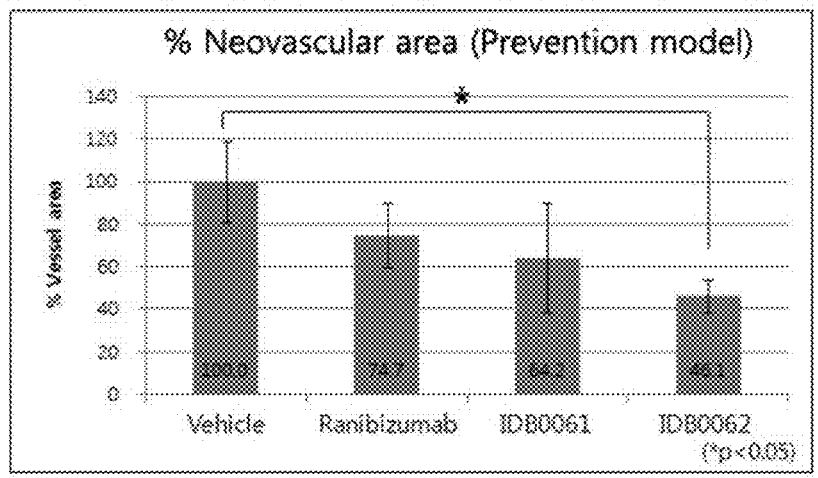
FIG. 6B is a graph obtained by quantifying the results of FIG. 6A.

As shown in FIG. 6, the prevention model experiment results confirmed that IDB0062 further inhibited neovascularization by 25-30% in comparison with ranibizumab, showing a significant preventive effect of 50% or more in comparison with vehicle, while IDB0061 also showed the equivalent efficacy in comparison with ranibizumab, indicating that the decrease in VEGF binding ability due to the structural change of ranibizumab did not substantially affect its neovascularization inhibitory efficacy and that the improvement of its efficacy could be attained by TPP fused to its C-terminus.

5-2 Resistance Models

The resistance models were constructed by inducing an alkaline burn in the same manner as in the Prevention models, and were left for 10 days so that the corneal vascularization protruded sufficiently. The concentration and cycle of administration were the same as in the Prevention models. The administration was carried out for 10 days from 10 days after the alkaline burning, and the reduction degree of generated neovessels was compared between IDB0062 and ranibizumab (thereafter, the preparation of the corneal slide was the same as in the Prevention models).

As shown in FIG. 7A, the vessels were developed up to the cornea in the vehicle- and ranibizumab-treated groups, whereas the vessels were locally distributed only in the ocular limbus in the IDB0062-treated group, showing a reduction of neovessels in the IDB0062-treated group. In conclusion, IDB0062 showed a significant neovessel reducing activity of 30% or more compared with the vehicle, and showed two times or higher improvement in efficacy in comparison with ranibizumab which showed no significant efficacy (FIG. 7B). These results are similar to the results in the literature in which anti-VEGF aptamer and anti-PDGF antibody agent were co-administered (Jo et al., 2006. Am. J. Pathol.). Therefore, it was expected that IDB0062 is likely to induce eyesight improvement in about 70% of ranibizumab-administered patients of which eyesight had been maintained without eyesight improvement.

In addition, as shown in FIG. 7C, it was confirmed that the IDB0062-treated group showed a significant reduction in pericyte coverage by nearly 40% in comparison with the vehicle-treated group, and these results are similar to that of a PDGF inhibitor which is under development as a coadministering agent for the purpose of treating patients having resistance to existing drugs. Therefore, it is anticipated that IDB0062 can be applicable as a monotherapy for treating resistance which is known to occur in 45% of patients administered with anti-VEGF inhibitor.

Example 6

Evaluation of Efficacy of Ranibizumab Modified Form Using Choroidal Neovascularization Models Choroidal neovascularization (CNV), which corresponds to a model of age-related macular degeneration, was induced by laser-induced choroidal neovascularization, and the therapeutic effect of ranibizumab modified form IDB0062 was investigated.

Seven-week old male Brown Norway (BN) rats (SLC Japan, Tokyo, Japan) were acclimated for one week, and then anesthetized by peritoneal injection of pentobarbital sodium (Hanlim Pharm, 25 mg/kg). Thereafter, the pupil was dilated with 1% tropicamide eye drops, and then six photocoagulation spots were formed around the optic nerve head using a diode laser (wavelength, 532 nm; diameter, 100 µm; power, 150 mW; time period, 0.1 sec). The destruction of Bruch's membrane was verified by the formation of characteristic bubbles. The eyeballs with hemorrhage or no bubbles were excluded from the subsequent experimental procedures. After the photocoagulation treatment, the rats were randomly divided into five groups (10 rats per group) as shown in Table 6. Drugs were administered intraocularly at concentrations appropriate for respective groups using Hamilton syringe (Hamilton, USA). The same amount of vehicle was administered to the CNV group, and 100 µg/eye of ranibizumab was administered as control drug. Subjects with surgical damage caused by drug administration or subjects with lens opacities or the like were excluded from subsequent experimental procedures.

TABLE 6

Chorodal neovascularization model experimental groups

| Group | dose |
|---|---|
| Vehicle | Buffer only |
| Ranibizumab | 100 µg/eye |
| IDB0062 | 10 µg/eye |
|  | 50 µg/eye |
|  | 100 µg/eye |

The degree of choroidal neovascularization was evaluated 10 days after drug administration. The eyeball of each rat was extracted, and then incised at a region adjacent to the cornea and sclera under a microscope. Thereafter, the retina was taken off using posterior tissues of the eyeball, and then the conjunctival tissue comprising a subretinal region was isolated. The isolated tissue was fixed in 4% paraformaldehyde for 1 hour, washed with PBS, and then stirred in PBS comprising 5% Triton X-100 and 1% BSA for 3 hours. After washing again, isolectin B4 (Sigma), as an endothelial cell marker, dissolved at 1 mg/ml in PBS, was diluted 1:50, followed by reaction at 4° C. overnight. After washing with PBS containing 0.05% Tween 20 for 2 hours, streptavidin TRITC was diluted 1:500, followed by reaction at 37° C. for 4 hours, and then, after washing with PBS for 30 minutes, the tissue was observed under a fluorescent microscope (BX51, Olympus, Japan). The sizes of subretinal neovascular areas were analyzed using Image J software (NIH, USA).

Figure 10A:
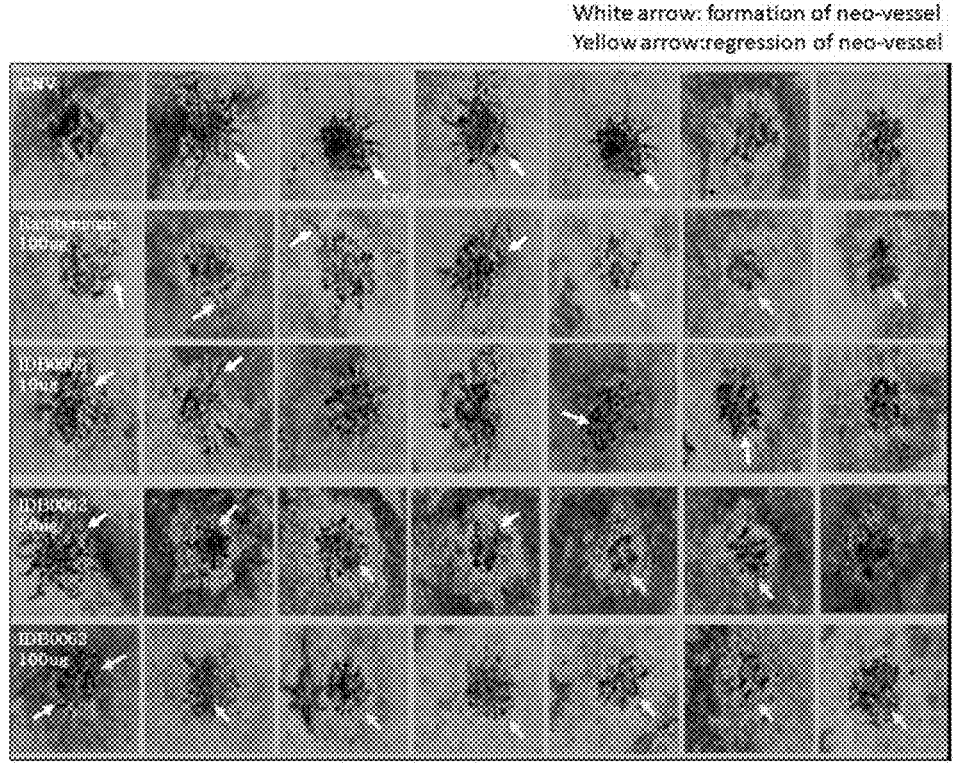
FIG. 10A shows an inhibitory aspect of choroidal neovascular proliferation by drug treatment of ranibizumab or a fusion protein according to the present invention in choroidal neovascularization (CNV) models.
Figure 10B:
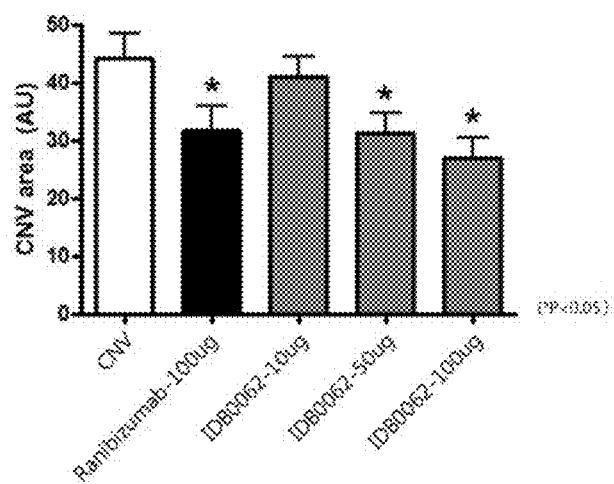
FIG. 10B is a graph obtained by quantifying the results of FIG. 10A.

As shown in FIG. 10A, it was detected that, in the vehicle group, a lot of neovessels labeled with black color were stretched out from the inside (choroid) to the outside (retina) of the laser-injured area. In the group administered with 100 µg of control drug ranibizumab, compared with the vehicle group, neovascularization tended to be somewhat inhibited but vessels still stretching out were observed in some subjects. Whereas, it was confirmed that IDB0062 tended to inhibit neovascularization in a concentration-dependent manner. It was verified that the group administered with 50 µg of IDB0062 had neovascularization inhibitory efficacy at a similar level to the group administered with 100 µg of control drug ranibizumab. In the group administered with 100 µg of IDB0062, only the laser-induced scarring remained in the retina, and most of the neovascularization was inhibited. As shown in FIG. 10B obtained from the quantification of the above results, it was confirmed that vascularization was inhibited by about 31% in the group administered with 100 µg of ranibizumab and the group administered with 50 µg of IDB0062 in comparison with the vehicle group, and neovascularization was inhibited by about 36% in the group administered with 100 µg of IDB0062. In conclusion, it was verified that IDB0062 exhibited the same neovascularization inhibitory efficacy as ranibizumab using a half the dose of ranibizumab.

Example 7

Evaluation of Efficacy of Ranibizumab Modified Form Using Oxygen-Induced Retinopathy Models For retinopathy of prematurity models, oxygen-induced retinopathy (OIR) was induced, and the effect of ranibizumab modified form IDB0062 was investigated.

Mice burn by crossbreeding of 7- to 8-week old C57BL/6 purchased from Koatech were used as experimental animals. On day 7 after birth, mice (postnatal day 7, P7) were placed in an oxygen chamber, and the oxygen concentration in the chamber was adjusted and maintained at 75% (hyperoxia) for 5 days (P7 to P11). The illumination in the laboratory was turned on or off every 12 hours and the temperature was maintained at 24±2° C. The mice were fed with free access to feed and drinking water. After 5 days, the mice were exposed to inner air (normoxia) out of the chamber for 5 days (P12-P17) to induce retinal angiogenesis. For drug administration, the mice were randomly divided into five groups (10 mice per group) immediately after the exposure to normoxia on P12, as shown in Table 7. Drugs were administered intraocularly at concentrations appropriate for respective groups using Hamilton syringe (Hamilton, USA). The same amount of vehicle was administered to the OIR group, and 10 µg/eye of ranibizumab was administered as control drug. Subjects with surgical damage caused by drug administration or subjects with lens opacities or the like were excluded from subsequent experiment procedures.

TABLE 7 oxygen-induced retinopathy (OIR) model experimental groups

| Group | dose |
|---|---|
| Vehicle | Buffer only |
| Ranibizumab | 10 µg/eye |
| IDB0062 | 5 µg/eye |
|  | 10 µg/eye |
|  | 15 µg/eye |

The degree of retinal edema was evaluated on day 17 after birth. The mice were anesthetized by peritoneal injection of pentobarbital sodium (Hanlim Pharm, 25 mg/kg). After the abdomen was opened, 10 μl of dextran (FD40S-1G, Sigma; 50 mg/ml in PBS) was injected into the heart. After 10 minutes, eyeballs were extracted, and fixed in 4% paraformaldehyde for 10 minutes, and then the retina was isolated. Thereafter, flat-mounted retina slides were prepared, and observed under a fluorescent microscope (BX51, Olympus, Japan). The amount of fluorescence extravasated out of vessels was quantitatively analyzed using Image J.

Figure 11A:
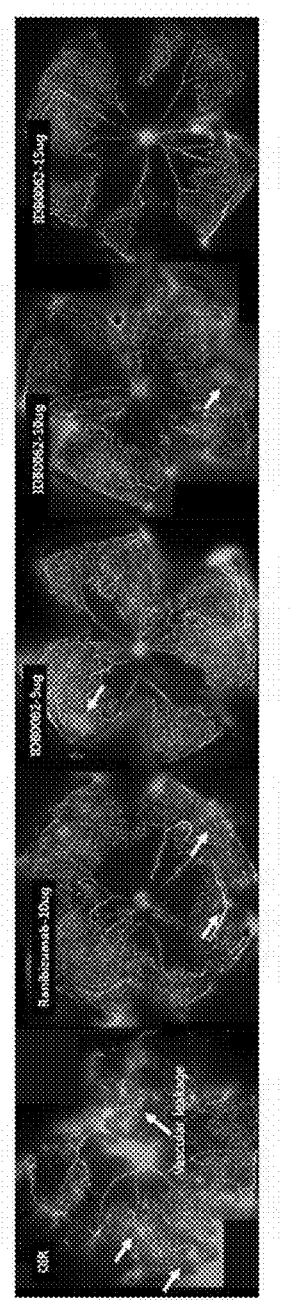
FIG. 11A shows the analysis results of the inhibition of leakage at vascular terminals by drug treatment of ranibizumab or a fusion protein according to the present invention in oxygen-induced retinopathy (OIR) models.
Figure 11B:
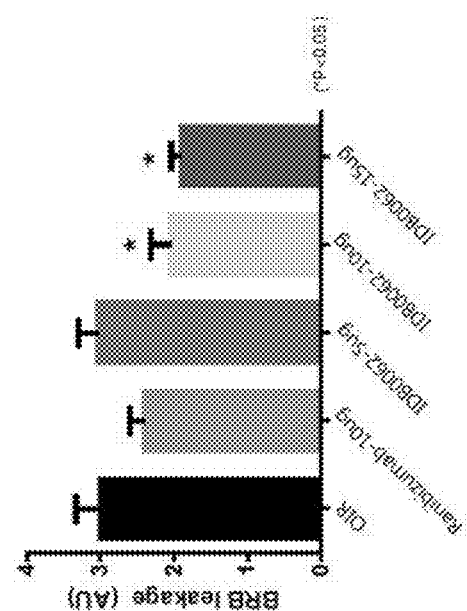
FIG. 11B is a graph obtained by quantifying the results of FIG. 11A.

As shown in FIG. 11A, it was detected that, in the vehicle group treated without drug, fluorescence extravasation due to leakage was increased in the optic nerve disc area at the center part and the vascular terminal area outside of the retina. In the group treated with 10 μg of control drug ranibizumab, compared to the vehicle group, vascular leakage were somewhat reduced, but fluorescence extravasation due to leaked vessels was still somewhat present in the vascular terminal area. Whereas, it was detected that the group treated with IDB0062 showed a tendency of inhibiting vascular leakage in a concentration-dependent manner, and the groups administered with IDB0062 (at least 10 μg, corresponding to the same dose of ranibizumab), although not statistically significant, had a possibility of inhibiting vascular leakage more effectively compared with ranibizumab (FIG. 11B). Especially, in the group administered with 15 μg of IDB0062, the shape of vessels has a dense and stable structure and the leaked area was not shown at all.

In addition, the extent of neovascularization in the retina was also evaluated. The isolated retina was fixed in 4% paraformaldehyde for 3 hour, washed with PBS, and then stirred in PBS containing 5% Triton X-100 and 1% BSA for 3 hours. After washing again, isolectin B4 (L2140, sigma) dissolved at 1 mg/ml in PBS was diluted 1:50, followed by reaction at 4° C. overnight. After washing with PBS containing 0.05% Tween 20 for 2 hours, streptavidin TRITC was diluted 1:500, followed by reaction at 37° C. for 4 hours, and then, after washing with PBS for 30 minutes, the tissue was observed under a fluorescent microscope (BX51, Olympus, Japan).

Figure 12A:
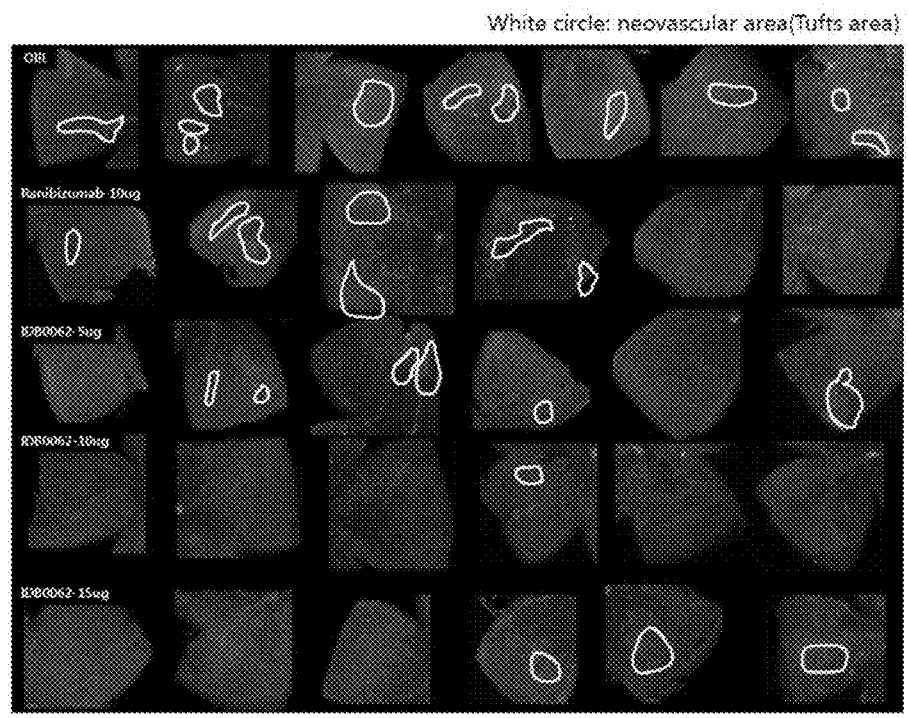
FIG. 12A shows the analysis results of the inhibition of the formation of neovascular and vascular tufts by drug treatment of ranibizumab or a fusion protein according to the present invention in oxygen-induced retinopathy (OIR) models using a fluorescent microscope after isolectin B4 staining.
Figure 12B:
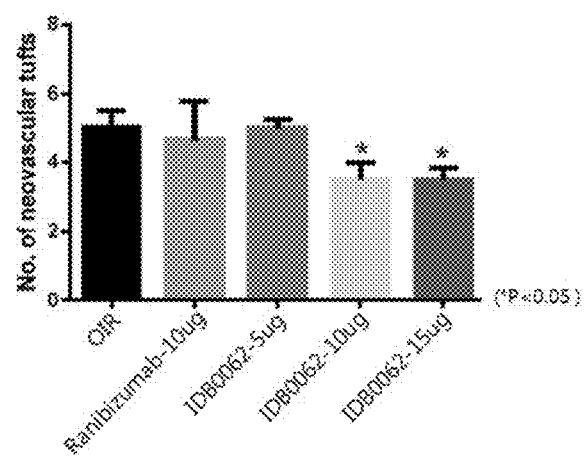
FIG. 12B is a graph obtained by quantifying the results of FIG. 12A.

When P7 mice were in hyperoxia condition for 5 days and then transferred to normoxia, P7 mice were in a relative ischemia state. Here, excessive neovessels grew in the retina, and the features of the formed neovessels were that the vessels grew from the retina toward the vitreous body corresponding to an avascular area and a specific structure called tufts having a form of irregular vessels that is easy to leak was formed. The formation of such tufts may be used as a measure to quantify neovascularization. As can be confirmed in FIG. 12A, in the stained vessels of the vehicle group, the boundaries between the vessels are clearly distinguished from each other, and the vessels exhibit characteristics of normal retinal vessels with a relatively thin and stable structure, whereas many neovessels that form tufts through gathering of irregular and thick vessels were observed. It was confirmed that, similar to the vehicle group, many neovessels in a form of tufts were distributed in the group treated with 10 μg of control drug ranibizumab. Whereas, IDB0062 significantly reduced the distribution of tufts, defined as neovessels, in a concentration-dependent manner, and, in the groups administered with 10 μg or more, most vascular structures were clearly distinguished from each other, and dense and tough normal vascular forms were observed rather than a tuft form. It was confirmed from a graph obtained by quantifying the results that all of the vehicle group, the group treated with 10 μg of ranibizumab, and the group administered with 5 μg of IDB0062 showed the same degree of neovascularization, but the group administered with 10 μg of IDB0062 inhibited neovascularization by about 40% in comparison with the above groups (FIG. 12B). In conclusion, it was confirmed that, in the OIR models, the treatment with rabinizumab did not show retinal neovascularization inhibitory efficacy, whereas IDB0062 could significantly inhibit OIR-induced neovascularization at the same dose as ranibizumab.

Example 8

Assay of Distribution of Drug after Intraocular Injection

In order to investigate the distribution of drug in the tissue when ranibizumab and IDB0062 were intraocularly injected, respectively, proteins were extracted from the retinal tissue and Western blot assay was performed.

The eye of each rat was extracted and then the retina was isolated 4 hours and 72 hours after the intraocular injection. The isolated retina was washed three times with PBS, and then transferred to lysis buffer (20 mM Tris-Cl, 150 mM NaCl, 1 mM EDTA, 0.1% triton X-100), and the tissues were disrupted using a homogenizer. Thereafter, supernatant was collected by centrifugation (14,000 rpm, 4° C., 10 min), and the protein contents of lysate was measured by Bradford assay. For Western blot assay, 12% non-reducing SDS-PAGE gel was used. Protein sample was loaded at 40 μg per well, and run at 25 mA for 1 hour. After transferring to PVDF membrane, proteins were detected using anti-kappa antibody-HRP (Sigma, F3761), and each protein band was quantified using Bio-Rad Chemidoc system.

Figure 13A:
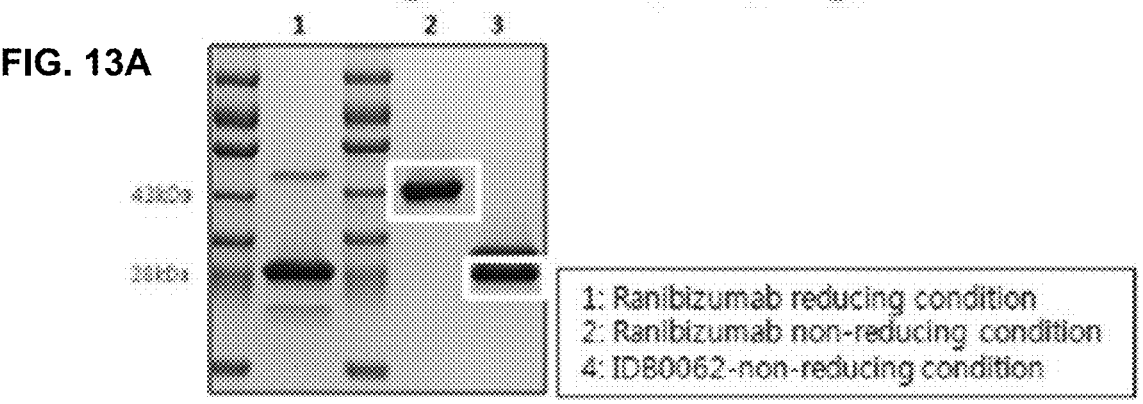
FIG. 13A shows the results of SDS-PAGE analysis of IDB0062 and ranibizumab and FIG. 13B shows the western blot analysis results of the amount of drug present in retinal tissues according to the time after the intraocular injection of IDB0062 and ranibizumab into rats.
Figure 13B:
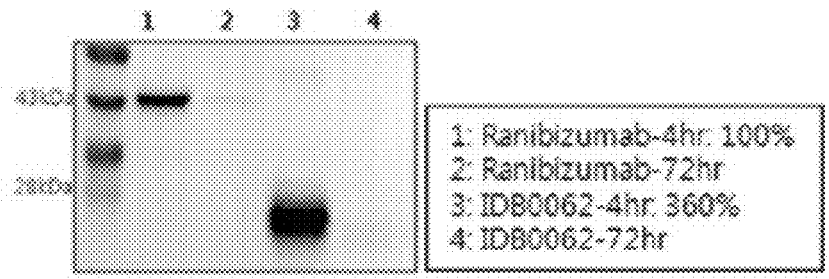

Since the heavy chain and the light chain of ranibizumab are linked by a disulfide bond, one band was observed at about 48 kDa in non-reducing SDS-PAGE. Whereas IDB0062 does not have a disulfide bond between the heavy chain and the light chain, and thus, two bands (heavy chain and light chain) were observed at 28 kDa in SDS-PAGE analysis. As shown in FIG. 13, it was verified that, as for the amount of drug present in the retina after 4 hours of the intraocular injection, IDB0062 was about 3.6 times higher than ranibizumab. These results indicate that IDB0062 specifically binds to the NRP1-expressing tissue by TPP, showing that IDB0062 can target the retinal tissue, which is a disease site with respect to various diseases caused by retinal neovascularization. In the intraocular injection of drug, a drug binding to a lesion tissue rather than a drug spread in the vitreous body has an increased opportunity to remove VEGF, so that the drug is likely to exert the same efficacy with a smaller dose. These results are presumed to support superior efficacy of IDB0062 in the efficacy evaluation using choroidal neovascularization models and retinopathy models.

INDUSTRIAL APPLICABILITY

In comparison with existing anti-vascular endothelial growth factor agents, the pharmaceutical compositions according to the present invention comprising, as an active ingredient, a fusion protein in which a tissue-penetrating peptide is fused to an anti-vascular endothelial growth factor (anti-VEGF) agent can inhibit various growth factors related to neovascularization as well as endothelial growth factors, reduce pericyte coverage to improve efficacy, and treat even drug-resistant patients. In addition, the pharmaceutical compositions of the present invention are highly industrial applicable in that the delivery capability of drug into the choroidal tissue is improved at the intraocular injection, so that the drug is highly likely to be developed as eye drops through a reduction in dose, an increase in the frequency of administration, and an improvement in ocular penetration.

The invention claimed is:

1. A ranibizumab mutant comprising the light chain amino acid sequence SEQ ID NO: 8 and the heavy chain amino acid sequence SEQ ID NO: 10.

2. A fusion protein comprising a tissue-penetrating peptide and the ranibizumab mutant of claim 1,
wherein the tissue-penetrating peptide comprises the amino acid sequence selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7.

3. The fusion protein of claim 2, wherein the tissue-penetrating peptide and the ranibizumab mutant are fused via a linker.

4. The fusion protein of claim 3, wherein the fusion protein comprises the amino acid sequence SEQ ID NO: 12 and the amino acid sequence SEQ ID NO: 14.

5. A method for inhibiting a neovascularization-induced eye disease in a subject in need thereof, comprising administering intraocularly to an affected eye of the subject a composition comprising a fusion protein and a pharmaceutically acceptable additive in an amount effective for inhibiting the neovascularization-induced eye disease in the affected eye of the subject, wherein the fusion protein comprises a tissue-penetrating peptide fused to a ranibizumab mutant comprising the light chain amino acid sequence SEQ ID NO: 8 and the heavy chain amino acid sequence SEQ ID NO: 10, wherein the tissue-penetrating peptide comprises the amino acid sequence selected from the group consisting of SEQ ID NO: 1, SEQ ID NO: 3, SEQ ID NO: 4, SEQ ID NO: 5, SEQ ID NO: 6, and SEQ ID NO: 7.

6. The method of claim 5, wherein the neovascularization-induced eye disease is selected from the group consisting of proliferative vitreoretinopathy, macular degeneration, pigmentary retinopathy, diabetic retinopathy, choroidal neovascularization, neovascular glaucoma, ischemic optic neuropathy, retinopathy of prematurity, retinopathy of immaturity, epidemic conjunctivitis, neovascular iris disease, retrolental fibroplasias, atopic keratitis, superior limbic keratitis, pterygium keratitis sicca, phlyctenular keratoconjunctivitis, scleritis, and diabetic macular edema.

7. The method of claim 5, wherein the fusion protein comprises the amino acid sequence SEQ ID NO: 12 and the amino acid sequence SEQ ID NO: 14.

8. A composition comprising-(a) a fusion protein comprising a ranibizumab mutant and a tissue-penetrating peptide, and (b) a pharmaceutically acceptable additive,
   wherein the ranibizumab mutant comprises a light chain amino acid sequence SEQ ID NO: 8 and a heavy chain amino acid sequence SEQ ID NO: 10, and
   wherein the tissue-penetrating peptide comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7.

9. The composition of claim 8, wherein the fusion protein comprises the amino acid sequence SEQ ID NO: 12 and the amino acid sequence SEQ ID NO: 14.

\* \* \* \* \*

SEQUENCE LISTING

<160> NUMBER OF SEQ ID NOS: 46

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      Tissue penetrating peptide(TPP)#1

<400> SEQUENCE: 1

His Thr Pro Gly Asn Ser Asn Lys Trp Lys His Leu Gln Glu Asn Lys
1               5                   10                  15

Lys Gly Arg Asn Arg Arg
            20

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      Tissue penetrating peptide(TPP)#2

<400> SEQUENCE: 2

His Thr Pro Gly Asn Ser Asn Lys Trp Lys His Leu Gln Glu Asn Lys
1               5                   10                  15

Lys Gly Arg Pro Arg Arg
            20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      Tissue penetrating peptide(TPP)#3

<400> SEQUENCE: 3

Arg Glu Ala Pro Gly Ala Pro Arg Ser Pro Glu Pro Gln Asp Gln Lys
1               5                   10                  15

Lys Pro Arg Asn Arg Arg
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      Tissue penetrating peptide(TPP)#4

<400> SEQUENCE: 4

Arg Glu Ala Pro Gly Ala Pro Arg Ser Pro Glu Pro Gln Asp Gln Lys
1               5                   10                  15

Lys Pro Arg Pro Arg Arg
            20

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      Tissue penetrating peptide(TPP)#5

```
<400> SEQUENCE: 5

His Thr Pro Gly Asn Ser Lys Pro Thr Arg Thr Pro Arg Arg
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      Tissue penetrating peptide(TPP)#6

<400> SEQUENCE: 6

His Thr Pro Gly Asn Ser Asn Gln Phe Val Leu Thr Ser Thr Arg Pro
1               5                   10                  15

Pro Arg

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      Tissue penetrating peptide(TPP)#7

<400> SEQUENCE: 7

His Thr Pro Gly Ile Ala Thr Arg Thr Pro Arg
1               5                   10

<210> SEQ ID NO 8
<211> LENGTH: 214
<212> TYPE: PRT
<213> ORGANISM: Artificial Sequence
<220> FEATURE:
<223> OTHER INFORMATION: Description of Artificial Sequence: Synthetic
      Ranibizumab mutant (IDB0061) light chain

<400> SEQUENCE: 8

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser
    210

<210> SEQ ID NO 9
<211> LENGTH: 642
<212> TYPE: DNA
<213> ORGANISM: Artificial Sequence
<220> FEATURE:
<223> OTHER INFORMATION: Description of Artificial Sequence: Synthetic
      Ranibizumab mutant (IDB0061) light chain

<400> SEQUENCE: 9
gatatccagt tgacgcagtc tccaagctcc ctgtctgcct ctgtggggga tcgtgtgacc      60
atcacctgca gcgccagcca ggatattagc aactatttaa actggtacca gcagaaacct    120
ggcaaagctc ccaaagttct catctatttc acctcctctc tgcactctgg tgtcccatct    180
cgcttcagtg gcagtggttc tgggacagac ttcactctca ctatcagcag cctgcagcct    240
gaagattttg caacttacta ttgtcaacag tatagcaccg tgccgtggac gttcggccaa    300
gggaccaagg tggaaatcaa acgtactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagttcgc ccgtcacaaa gagcttcaac aggggagagt ct                       642

<210> SEQ ID NO 10
<211> LENGTH: 231
<212> TYPE: PRT
<213> ORGANISM: Artificial Sequence
<220> FEATURE:
<223> OTHER INFORMATION: Description of Artificial Sequence: Synthetic
      Ranibizumab mutant (IDB0061) heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Glu Gly
    130                 135                 140

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Ser Asp Lys Thr His Leu
225                 230

<210> SEQ ID NO 11
<211> LENGTH: 693
<212> TYPE: DNA
<213> ORGANISM: Artificial Sequence
<220> FEATURE:
<223> OTHER INFORMATION: Description of Artificial Sequence: Synthetic
      Ranibizumab mutant (IDB0061) heavy chain

<400> SEQUENCE: 11
gaagtgcagc tggtggagtc tgggggaggc ctggtccagc ctgggggtc cctgagactc       60 tcctgtgcag cctctggata tgatttcacc cattatggta tgaattgggt ccgccaggct     120
ccagggaagg ggctggagtg ggtcggctgg attaacacct ataccggtga accgacctac     180
gcagcggatt tcaagcgtcg attcaccttt tccctggaca ccagcaagtc aacggcgtat     240
ctacaaatga acagcctgag agccgaggac acggccgtct attactgtgc gaaatacccg     300
tattactatg gtaccagcca ctggtatttc gacgtctggg gccaaggaac cctggtcacc     360
gtctcctcag cctccaccaa gggcccatcg gtcttccccc tggcaccctc ctccaagagc     420
acctctgagg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca acaccaaggt ggacaagaaa     660
gttgagccca atcttctga caaaacccac ctg                                   693

<210> SEQ ID NO 12
<211> LENGTH: 251
<212> TYPE: PRT
<213> ORGANISM: Artificial Sequence
<220> FEATURE:
<223> OTHER INFORMATION: Description of Artificial Sequence: Synthetic
      Fusion protein (IDB0062) light chain

<400> SEQUENCE: 12

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Gly Gly Gly Ser Gly Gly Gly Ser
    210                 215                 220

Gly Gly Gly Gly Ser His Thr Pro Gly Asn Ser Asn Lys Trp Lys His
225                 230                 235                 240

Leu Gln Glu Asn Lys Lys Gly Arg Pro Arg Arg
                245                 250

<210> SEQ ID NO 13
<211> LENGTH: 753
<212> TYPE: DNA
<213> ORGANISM: Artificial Sequence
<220> FEATURE:
<223> OTHER INFORMATION: Description of Artificial Sequence: Synthetic
      Fusion protein (IDB0062) light chain

<400> SEQUENCE: 13
gatatccagt tgacgcagtc tccaagctcc ctgtctgcct ctgtggggga tcgtgtgacc        60
atcacctgca gcgccagcca ggatattagc aactatttaa actggtacca gcagaaacct       120
ggcaaagctc ccaaagttct catctatttc acctcctctc tgcactctgg tgtcccatct       180
cgcttcagtg gcagtggttc tgggacagac ttcactctca ctatcagcag cctgcagcct       240
gaagattttg caacttacta ttgtcaacag tatagcaccg tgccgtggac gttcggccaa       300
gggaccaagg tggaaatcaa acgtactgtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag cacccctgacg      540 ctgagcaaag cagactacga aaacacaaa gtctacgcct gcgaagtcac ccatcagggc        600
ctgagttcgc ccgtcacaaa gagcttcaac agggagagt ctggtggcgg tggctctggt        660
ggcggtggca gcggtggcgg tggctctcac accccgggta actctaacaa atggaaacac       720
ctgcaggaaa acaaaaaagg tcgtccgcgt cgt                                    753

<210> SEQ ID NO 14
<211> LENGTH: 268
<212> TYPE: PRT
<213> ORGANISM: Artificial Sequence
<220> FEATURE:
<223> OTHER INFORMATION: Description of Artificial Sequence: Synthetic
      Fusion protein (IDB0062) heavy chain

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Glu Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Ser Asp Lys Thr His Leu Gly Gly Gly Ser Gly Gly Gly Gly Gly
225                 230                 235                 240

Ser Gly Gly Gly Gly Ser His Thr Pro Gly Asn Ser Asn Lys Trp Lys
                245                 250                 255

His Leu Gln Glu Asn Lys Lys Gly Arg Pro Arg Arg
            260                 265
```

<210> SEQ ID NO 15
<211> LENGTH: 804
<212> TYPE: DNA
<213> ORGANISM: Artificial Sequence
<220> FEATURE:
<223> OTHER INFORMATION: Description of Artificial Sequence: Synthetic Fusion protein (IDB0062) heavy chain

<400> SEQUENCE: 15

```
gaagtgcagc tggtggagtc tgggggaggc ctggtccagc ctggggggtc cctgagactc      60
tcctgtgcag cctctggata tgatttcacc cattatggta tgaattgggt ccgccaggct     120
ccagggaagg gctggagtg gtcggctgg attaacacct ataccggtga accgacctac       180
gcagcggatt tcaagcgtcg attcaccttt tccctggaca ccagcaagtc aacggcgtat     240
ctacaaatga acagcctgag agccgaggac acggccgtct attactgtgc gaaatacccg     300
tattactatg gtaccagcca ctggtatttc gacgtctggg gccaaggaac cctggtcacc     360
gtctcctcag cctccaccaa gggcccatcg gtcttccccc tggcaccctc ctccaagagc     420
```

```
acctctgagg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaaa    660
gttgagccca atcttctga caaaacccac ctgggtggcg gtggctctgg tggcggtggc    720
agcggtggcg gtggctctca ccccgggt aactctaaca aatggaaaca cctgcaggaa    780
aacaaaaaag gtcgtccgcg tcgt                                           804
```

<210> SEQ ID NO 16
<211> LENGTH: 243
<212> TYPE: PRT
<213> ORGANISM: Artificial Sequence
<220> FEATURE:
<223> OTHER INFORMATION: Description of Artificial Sequence: Synthetic
      Fusion protein (IDB0064) light chain

<400> SEQUENCE: 16

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Gly Gly Gly Ser Gly Gly Gly Gly Ser
    210                 215                 220

Gly Gly Gly Gly Ser His Thr Pro Gly Asn Ser Lys Pro Thr Arg Thr
225                 230                 235                 240

Pro Arg Arg
```

<210> SEQ ID NO 17
<211> LENGTH: 729
<212> TYPE: DNA
<213> ORGANISM: Artificial Sequence
<220> FEATURE:
<223> OTHER INFORMATION: Description of Artificial Sequence: Synthetic Fusion protein (IDB0064) light chain

<400> SEQUENCE: 17

```
gatatccagt tgacgcagtc tccaagctcc ctgtctgcct ctgtggggga tcgtgtgacc    60
atcacctgca gcgccagcca ggatattagc aactatttaa actggtacca gcagaaacct   120
ggcaaagctc ccaaagttct catctatttc acctcctctc tgcactctgg tgtcccatct   180
cgcttcagtg gcagtggttc tgggacagac ttcactctca ctatcagcag cctgcagcct   240
gaagattttg caacttacta ttgtcaacag tatagcaccg tgccgtggac gttcggccaa   300
gggaccaagg tggaaatcaa acgtactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagttcgc ccgtcacaaa gagcttcaac aggggagagt ctggtggcgg tggctctggt   660
ggcggtggca gcggtggcgg tggctctcat actcctggaa atagcaaacc aacacgcaca   720
ccaaggcgt                                                            729
```

<210> SEQ ID NO 18
<211> LENGTH: 260
<212> TYPE: PRT
<213> ORGANISM: Artificial Sequence
<220> FEATURE:
<223> OTHER INFORMATION: Description of Artificial Sequence: Synthetic
      Fusion protein (IDB0064) heavy chain

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Glu Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

Asn His Lys Pro Ser Asn Thr Lys Val Asp Lys Val Glu Pro Lys
            210                 215                 220

Ser Ser Asp Lys Thr His Leu Gly Gly Gly Ser Gly Gly Gly Gly
225                 230                 235                 240

Ser Gly Gly Gly Ser His Thr Pro Gly Asn Ser Lys Pro Thr Arg
                245                 250                 255

Thr Pro Arg Arg
            260

<210> SEQ ID NO 19
<211> LENGTH: 780
<212> TYPE: DNA
<213> ORGANISM: Artificial Sequence
<220> FEATURE:
<223> OTHER INFORMATION: Description of Artificial Sequence: Synthetic
      Fusion protein (IDB0064) heavy chain

<400> SEQUENCE: 19
gaagtgcagc tggtggagtc tgggggaggc ctggtccagc ctggggggtc cctgagactc        60
tcctgtgcag cctctggata tgatttcacc cattatggta tgaattgggt ccgccaggct       120
ccagggaagg ggctggagtg ggtcggctgg attaacacct ataccggtga accgacctac       180
gcagcggatt tcaagcgtcg attcaccttt tccctggaca ccagcaagtc aacggcgtat       240
ctacaaatga acagcctgag agccgaggac acggccgtct attactgtgc gaatacccg        300 tattactatg gtaccagcca ctggtatttc gacgtctggg gccaaggaac cctggtcacc       360
gtctcctcag cctccaccaa gggcccatcg gtcttccccc tggcaccctc ctccaagagc       420
acctctgagg gcacagcggc cctgggctgc ctggtcaagg actacttccc cgaaccggtg       480
acggtgtcgt ggaactcagg cgccctgacc agcggcgtgc acaccttccc ggctgtccta       540
cagtcctcag gactctactc cctcagcagc gtggtgaccg tgccctccag cagcttgggc       600
acccagacct acatctgcaa cgtgaatcac aagcccagca acaccaaggt ggacaagaaa       660
gttgagccca atcttctga caaaacccac ctgggtggcg gtggctctgg tggcggtggc       720
agcggtggcg gtggctctca tactcctgga aatagcaaac caacacgcac accaaggcgt       780

<210> SEQ ID NO 20
<211> LENGTH: 233
<212> TYPE: PRT
<213> ORGANISM: Artificial Sequence
<220> FEATURE:
<223> OTHER INFORMATION: Description of Artificial Sequence: Synthetic
      Fusion protein (IDB0072) light chain

<400> SEQUENCE: 20

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Ser Ala Ser Gln Asp Ile
        35                  40                  45

Ser Asn Tyr Leu Asn Trp Tyr Gln Gln Lys Pro Gly Lys Ala Pro Lys
    50                  55                  60

Val Leu Ile Tyr Phe Thr Ser Ser Leu His Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Ser Thr
                100                 105                 110

Val Pro Trp Thr Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 21
<211> LENGTH: 699
<212> TYPE: DNA
<213> ORGANISM: Artificial Sequence
<220> FEATURE:
<223> OTHER INFORMATION: Description of Artificial Sequence: Synthetic
      Fusion protein (IDB0072) light chain

<400> SEQUENCE: 21
atgggctggt cctgcatcat cctgttcctg gtggccaccg ccaccggcgt gcactccgac      60
atccagatga cccagtcccc ctcctccctg tccgcctccg tgggcgaccg ggtgaccatc     120
acctgctccg cctcccagga catctccaac tacctgaact ggtaccagca gaagcccggc     180
aaggccccca aggtgctgat ctacttcacc tcctccctgc actccggcgt gccctcccgg     240
ttctccggct ccggctccgg caccgacttc accctgacca tctcctccct gcagcccgag     300
gacttcgcca cctactactg ccagcagtac tccaccgtgc cctggacctt cggccagggc     360
accaaggtgg agatcaagcg gaccgtggcc gccccctccg tgttcatctt cccccctcc     420 gacgagcagc tgaagtccgg caccgcctcc gtggtgtgcc tgctgaacaa cttctacccc     480
cgggaggcca aggtgcagtg gaaggtggac aacgccctgc agtccggcaa ctcccaggag     540
tccgtgaccg agcaggactc caaggactcc acctactccc tgtcctccac cctgaccctg     600
tccaaggccg actacgagaa gcacaaggtg tacgcctgcg aggtgaccca ccagggcctg     660
tcctcccccg tgaccaagtc cttcaaccgg ggcgagtgc                            699

<210> SEQ ID NO 22
<211> LENGTH: 508
<212> TYPE: PRT
<213> ORGANISM: Artificial Sequence
<220> FEATURE:
<223> OTHER INFORMATION: Description of Artificial Sequence: Synthetic
      Fusion protein (IDB0072) heavy chain

<400> SEQUENCE: 22

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

-continued

```
Pro Gly Gly Ser Leu Arg Leu Ser Cys Ala Ala Ser Gly Tyr Thr Phe
             35                  40                  45
Thr Asn Tyr Gly Met Asn Trp Val Arg Gln Ala Pro Gly Lys Gly Leu
 50                  55                  60
Glu Trp Val Gly Trp Ile Asn Thr Tyr Thr Gly Glu Pro Thr Tyr Ala
 65                  70                  75                  80
Ala Asp Phe Lys Arg Arg Phe Thr Phe Ser Leu Asp Thr Ser Lys Ser
                 85                  90                  95
Thr Ala Tyr Leu Gln Met Asn Ser Leu Arg Ala Glu Asp Thr Ala Val
             100                 105                 110
Tyr Tyr Cys Ala Lys Tyr Pro His Tyr Tyr Gly Ser Ser His Trp Tyr
         115                 120                 125
Phe Asp Val Trp Gly Gln Gly Thr Leu Val Thr Val Ser Ser Ala Ser
130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                 165                 170                 175
Glu Pro Val Thr Val Ser Trp Asn Ser Gly Ala Leu Thr Ser Gly Val
             180                 185                 190
His Thr Phe Pro Ala Val Leu Gln Ser Ser Gly Leu Tyr Ser Leu Ser
         195                 200                 205
Ser Val Val Thr Val Pro Ser Ser Leu Gly Thr Gln Thr Tyr Ile
     210                 215                 220
Cys Asn Val Asn His Lys Pro Ser Asn Thr Lys Val Asp Lys Lys Val
225                 230                 235                 240
Glu Pro Lys Ser Cys Asp Lys Thr His Thr Cys Pro Pro Cys Pro Ala
                 245                 250                 255
Pro Glu Leu Leu Gly Gly Pro Ser Val Phe Leu Phe Pro Pro Lys Pro
             260                 265                 270
Lys Asp Thr Leu Met Ile Ser Arg Thr Pro Glu Val Thr Cys Val Val
         275                 280                 285
Val Asp Val Ser His Glu Asp Pro Glu Val Lys Phe Asn Trp Tyr Val
290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                 325                 330                 335
Asp Trp Leu Asn Gly Lys Glu Tyr Lys Cys Lys Val Ser Asn Lys Ala
             340                 345                 350
Leu Pro Ala Pro Ile Glu Lys Thr Ile Ser Lys Ala Lys Gly Gln Pro
         355                 360                 365
Arg Glu Pro Gln Val Tyr Thr Leu Pro Pro Ser Arg Asp Glu Leu Thr
370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                 405                 410                 415
Lys Thr Thr Pro Pro Val Leu Asp Ser Asp Gly Ser Phe Phe Leu Tyr
             420                 425                 430
Ser Lys Leu Thr Val Asp Lys Ser Arg Trp Gln Gln Gly Asn Val Phe
         435                 440                 445
Ser Cys Ser Val Met His Glu Ala Leu His Asn His Tyr Thr Gln Lys
```

```
                450           455           460
Ser Leu Ser Leu Ser Pro Gly Lys Gly Gly Gly Ser Gly Gly
465                 470               475                 480

Gly Ser Gly Gly Gly Gly Ser His Thr Pro Gly Asn Ser Asn Gln His
                    485               490                 495

Ala His Gln Gly Val Glu Tyr Pro Glu Lys Asp Gln
            500               505
```

<210> SEQ ID NO 23
<211> LENGTH: 1524
<212> TYPE: DNA
<213> ORGANISM: Artificial Sequence
<220> FEATURE:
<223> OTHER INFORMATION: Description of Artificial Sequence: Synthetic
      Fusion protein (IDB0072) heavy chain

<400> SEQUENCE: 23

```
atgggctggt cctgcatcat cctgttcctg gtggccaccg ccaccggcgt gcactccgag    60
gtgcagctgg tggagtccgg cggcggcctg gtgcagcccg gcggctccct gcggctgtcc   120
tgcgccgcct ccggctacac cttcaccaac tacggcatga actgggtgcg gcaggccccc   180
ggcaagggcc tggagtgggt gggctggatc aacacctaca ccggcgagcc cacctacgcc   240
gccgacttca gcggcggtt  caccttctcc ctggacacct ccaagtccac cgcctacctg   300
cagatgaact ccctgcgggc cgaggacacc gccgtgtact actgcgccaa gtaccccac   360
tactacggct cctcccactg gtacttcgac gtgtggggcc agggcaccct ggtgaccgtg   420
tcctccgcct ccaccaaggg cccatcggtc ttccccctgg cacctcctc  caagagcacc   480
tctgggggca gcgcggccct gggctgcctg gtcaaggact acttccccga accggtgacg   540
gtgtcgtgga actcaggcgc cctgaccagc ggcgtgcaca ccttcccggc tgtcctacag   600
tcctcaggac tctactccct cagcagcgtg gtgaccgtgc cctccagcag cttgggcacc   660
cagacctaca tctgcaacgt gaatcacaag cccagcaaca ccaaggtgga caagaaagtt   720
gagcccaaat cttgtgacaa aactcacaca tgcccaccgt gcccagcacc tgaactcctg   780
gggggaccgt cagtcttcct cttccccca  aaacccaagg acaccctcat gatctcccgg   840
acccctgagg tcacatgcgt ggtggtggac gtgagccacg aagaccctga ggtcaagttc   900
aactggtacg tggacggcgt ggaggtgcat aatgccaaga caaagccgcg ggaggagcag   960
tacaacagca cgtaccgtgt ggtcagcgtc ctcaccgtcc tgcaccagga ctggctgaat  1020
ggcaaggagt acaagtgcaa ggtctccaac aaagccctcc cagcccccat cgagaaaacc  1080
atctccaaag ccaaagggca gccccgagaa ccacaggtgt acaccctgcc cccatcccgg  1140
gatgagctga ccaagaacca ggtcagcctg acctgcctgg tcaaaggctt ctatcccagc  1200
gacatcgccg tggagtggga gagcaatggg cagccggaga caactacaa  gaccacgcct  1260
cccgtgctgg actccgacgg ctccttcttc ctctacagca agctcaccgt ggacaagagc  1320
aggtggcagc aggggaacgt cttctcatgc tccgtgatgc atgaggctct gcacaaccac  1380
tacacgcaga agagcctctc cctgtccccg ggtaaaggtg aggaggatc  tggaggagga  1440
ggaagtggag gtgaggatc  acatactcct ggaaatagca accaacacgc acaccaaggc  1500
gttgaatatc ccgagaagga tcaa                                        1524
```

<210> SEQ ID NO 24
<211> LENGTH: 25
<212> TYPE: DNA
<213> ORGANISM: Artificial Sequence

```
<220> FEATURE:
<223> OTHER INFORMATION: Description of Artificial Sequence: Synthetic
      Cloning primer#1

<400> SEQUENCE: 24
tgtggctgca ccatctgtct tcatc                                            25

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      Cloning primer#2

<400> SEQUENCE: 25
agactctccc ctgttgaagc tctttgtg                                         28

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      Cloning primer#3

<400> SEQUENCE: 26
cacaaagagc ttcaacaggg gagagt                                           26

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      Cloning primer#4

<400> SEQUENCE: 27
ttaacgacgc ggacgacctt ttttgtttt                                        29

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      Cloning primer#5

<400> SEQUENCE: 28
atgaaaaaaa ctgcgattgc gattgcggt                                        29

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      Cloning primer#6

<400> SEQUENCE: 29
gatgaagaca gatggtgcag ccaca                                            25

<210> SEQ ID NO 30
<211> LENGTH: 38
<212> TYPE: DNA
<213> ORGANISM: Artificial Sequence
<220> FEATURE:
```

<223> OTHER INFORMATION: Description of Artificial Sequence: Synthetic
      Cloning primer#7

<400> SEQUENCE: 30
gggggatcca tgaaaaaaac tgcgattgcg attgcggt                          38

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      Cloning primer#8

<400> SEQUENCE: 31
gggctcgagt taacgacgcg gacgaccttt tttgtttt                          38

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      Cloning primer#9

<400> SEQUENCE: 32
gcctccacca agggcccatc                                             20

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      Cloning primer#10

<400> SEQUENCE: 33
agaagatttg ggctcaactt tcttgtccac                                  30

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      Cloning primer#11

<400> SEQUENCE: 34
gtggacaaga aagttgagcc caaatctt                                    28

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      Cloning primer#12

<400> SEQUENCE: 35
ttaacgacgc ggacgacctt ttttgtttt                                   29

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic Cloning primer#13

<400> SEQUENCE: 36
atgaaaaaac tgctgttcgc gattccgc        28

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      Cloning primer#14

<400> SEQUENCE: 37
cgatgggccc ttggtggagg        20

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      Cloning primer#15

<400> SEQUENCE: 38
ggggaattca tgaaaaaact gctgttcgcg attccgc        37

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic
      Cloning primer#16

<400> SEQUENCE: 39
gggaagcttt taacgacgcg gacgaccttt tttgtttt        38

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Synthetic
      Cloning primer#17

<400> SEQUENCE: 40
cccggatcca tgaaaaaaac tgcgattgcg attgcggt        38

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Synthetic
      Cloning primer#18

<400> SEQUENCE: 41
cccgaattca tgaaaaaact gctgttcgcg attccgc        37

<210> SEQ ID NO 42
<211> LENGTH: 59
<212> TYPE: DNA
<213> ORGANISM: Artificial Sequence
<220> FEATURE:
<223> OTHER INFORMATION: Description of Artificial Sequence: Synthetic
      Cloning primer#19

```
<400> SEQUENCE: 42
ggctctcaca ccccgggtaa ctctaaacca acacgcacac caaggcgtta actcgaggg      59

<210> SEQ ID NO 43
<211> LENGTH: 4
<212> TYPE: PRT
<213> ORGANISM: Artificial Sequence
<220> FEATURE:
<223> OTHER INFORMATION: Furin Protease
<220> FEATURE:
<221> NAME/KEY: misc_feature
<222> LOCATION: (2)..(2)
<223> OTHER INFORMATION: Xaa can be any naturally occurring amino acid

<400> SEQUENCE: 43

Arg Xaa Arg Arg
1

<210> SEQ ID NO 44
<211> LENGTH: 5
<212> TYPE: PRT
<213> ORGANISM: Artificial Sequence
<220> FEATURE:
<223> OTHER INFORMATION: Linker Peptide

<400> SEQUENCE: 44

Gly Gly Gly Gly Ser
1               5

<210> SEQ ID NO 45
<211> LENGTH: 15
<212> TYPE: PRT
<213> ORGANISM: Artificial Sequence
<220> FEATURE:
<223> OTHER INFORMATION: Linker Peptide

<400> SEQUENCE: 45

Gly Gly Gly Gly Ser Gly Gly Gly Gly Ser Gly Gly Gly Gly Ser
1               5                   10                  15

<210> SEQ ID NO 46
<211> LENGTH: 4
<212> TYPE: PRT
<213> ORGANISM: Artificial Sequence
<220> FEATURE:
<223> OTHER INFORMATION: Linker Peptide

<400> SEQUENCE: 46

Gly Ala Gly Ala
1
```